United States Patent
Moss et al.

(10) Patent No.: US 12,128,231 B2
(45) Date of Patent: *Oct. 29, 2024

(54) METHODS OF TREATMENT USING TREATMENT APPLICATOR WITH PROTECTED ELECTRODES

(71) Applicant: PULSE BIOSCIENCES, INC., Hayward, CA (US)

(72) Inventors: Kevin L. Moss, Lathrop, CA (US); Christopher J. Foster, San Francisco, CA (US); Cameron D. Hinman, Thurmond, NC (US); David J. Danitz, San Jose, CA (US); Darrin R. Uecker, San Mateo, CA (US)

(73) Assignee: Pulse Biosciences, Inc., Hayward, CA (US)

(*) Notice: Subject to any disclaimer, the term of this patent is extended or adjusted under 35 U.S.C. 154(b) by 244 days.

This patent is subject to a terminal disclaimer.

(21) Appl. No.: 17/398,637

(22) Filed: Aug. 10, 2021

(65) Prior Publication Data
US 2021/0370049 A1    Dec. 2, 2021

Related U.S. Application Data

(63) Continuation of application No. 16/247,469, filed on Jan. 14, 2019, now Pat. No. 11,167,125.
(Continued)

(51) Int. Cl.
*A61N 1/40* (2006.01)
*A61B 18/14* (2006.01)
(Continued)

(52) U.S. Cl.
CPC ............ *A61N 1/0502* (2013.01); *A61B 18/14* (2013.01); *A61B 34/32* (2016.02); *A61B 34/37* (2016.02);
(Continued)

(58) Field of Classification Search
CPC .................. A61B 18/1477; A61B 2018/00577
See application file for complete search history.

(56) References Cited

U.S. PATENT DOCUMENTS

| 4,043,342 A | 8/1977 | Morrison |
| 5,074,802 A | 12/1991 | Gratziani et al. |
| (Continued) | | |

FOREIGN PATENT DOCUMENTS

| CA | 2838411 A1 | 1/2005 |
| WO | WO99/06101 A1 | 2/1999 |
| (Continued) | | |

OTHER PUBLICATIONS

European Supplemental Search Report mailed Oct. 25, 2021 for European Patent Application No. 19741761.1; 11 pages.
(Continued)

*Primary Examiner* — Michael J D'Abreu
(74) *Attorney, Agent, or Firm* — Shay Glenn LLP

(57) ABSTRACT

Described herein are methods of treating a tissue using a treatment tip apparatus (e.g., devices, systems, etc.) including one, or more preferably a plurality, of electrodes that are protected by an electrode partition, such as an electrode housing (which may be retractable) until pressed against the tissue for deployment of the electrodes and delivery of a therapeutic treatment. In particular, these methods may include the use of a plurality of treatment electrodes (e.g., needle electrodes) and in some examples may include for the delivery of nanosecond pulsed electric fields.

22 Claims, 21 Drawing Sheets

Related U.S. Application Data

(60) Provisional application No. 62/618,022, filed on Jan. 16, 2018.

(51) Int. Cl.
*A61B 34/32* (2016.01)
*A61B 34/37* (2016.01)
*A61N 1/05* (2006.01)
*A61B 18/00* (2006.01)

(52) U.S. Cl.
CPC ...... *A61N 1/40* (2013.01); *A61B 2018/00702* (2013.01); *A61B 2018/1425* (2013.01); *A61B 2018/1432* (2013.01); *A61B 18/1445* (2013.01)

(56) References Cited

U.S. PATENT DOCUMENTS

| | | |
|---|---|---|
| 5,568,035 A | 10/1996 | Kato et al. |
| 5,635,776 A | 6/1997 | Imi |
| 5,688,253 A | 11/1997 | Paradis |
| 5,702,359 A | 12/1997 | Hofmann et al. |
| 5,718,246 A | 2/1998 | Vona |
| 5,735,827 A | 4/1998 | Adwers et al. |
| 5,769,827 A | 6/1998 | Demichele et al. |
| 5,774,348 A | 6/1998 | Druce et al. |
| 5,792,122 A | 8/1998 | Brimhall et al. |
| 5,798,579 A | 8/1998 | McPhee |
| 5,902,272 A | 5/1999 | Eggers et al. |
| 5,907,484 A | 5/1999 | Kowshik et al. |
| 6,008,690 A | 12/1999 | Takeshima et al. |
| 6,009,347 A | 12/1999 | Hofmann |
| 6,010,487 A | 1/2000 | Demichele et al. |
| 6,017,354 A | 1/2000 | Culp et al. |
| 6,026,003 A | 2/2000 | Moore et al. |
| 6,048,789 A | 4/2000 | Vines et al. |
| 6,137,276 A | 10/2000 | Rudolph |
| 6,181,964 B1 | 1/2001 | Hofmann et al. |
| 6,190,381 B1 | 2/2001 | Olsen et al. |
| 6,221,056 B1 | 4/2001 | Silverman |
| 6,246,200 B1 | 6/2001 | Blumenkranz et al. |
| 6,326,177 B1 | 12/2001 | Schoenbach et al. |
| 6,331,181 B1 | 12/2001 | Tierney et al. |
| 6,508,786 B2 | 1/2003 | Huitema et al. |
| 6,633,093 B1 | 10/2003 | Rim et al. |
| 6,654,636 B1 | 11/2003 | Dev et al. |
| 6,697,670 B2 | 2/2004 | Chomenky et al. |
| 6,743,211 B1 | 6/2004 | Prausnitz et al. |
| 6,770,081 B1 | 8/2004 | Cooper et al. |
| 6,831,377 B2 | 12/2004 | Yampolsky et al. |
| 7,395,112 B2 | 7/2008 | Keisari et al. |
| 7,496,401 B2 | 2/2009 | Bernabei |
| 7,666,191 B2 | 2/2010 | Orban et al. |
| 7,699,855 B2 | 4/2010 | Anderson et al. |
| 7,767,433 B2 | 8/2010 | Kuthi et al. |
| 7,855,904 B2 | 12/2010 | Kirbie et al. |
| RE42,277 E | 4/2011 | Jaafar et al. |
| 7,937,143 B2 | 5/2011 | Demarais et al. |
| 7,938,824 B2 | 5/2011 | Chomenky et al. |
| 8,000,813 B2 | 8/2011 | Schoenbach et al. |
| 8,216,224 B2 | 7/2012 | Morris et al. |
| 8,429,582 B1 | 4/2013 | Lai et al. |
| 8,512,334 B2 | 8/2013 | Nuccitelli et al. |
| 8,688,227 B2 | 4/2014 | Nuccitelli et al. |
| 8,814,833 B2 | 8/2014 | Farrell et al. |
| 8,822,222 B2 | 9/2014 | Beebe et al. |
| 8,852,208 B2 | 10/2014 | Gomez et al. |
| 8,979,912 B2 | 3/2015 | Na et al. |
| 9,101,337 B2 | 8/2015 | Hoegerle et al. |
| 9,101,764 B2 | 8/2015 | Nuccitelli et al. |
| 9,414,881 B2 | 8/2016 | Callas et al. |
| 9,629,991 B1 | 4/2017 | O'Brien et al. |
| 9,724,155 B2 | 8/2017 | Nuccitelli et al. |
| 9,895,520 B2 | 2/2018 | Burton et al. |
| 9,931,161 B2 | 4/2018 | Willis |
| 9,953,815 B2 | 4/2018 | Griebeler |
| 9,956,391 B2 | 5/2018 | Weissberg et al. |
| 9,960,763 B2 | 5/2018 | Miller et al. |
| 9,999,467 B2 | 6/2018 | Moss et al. |
| 10,020,800 B2 | 7/2018 | Prager et al. |
| 10,022,695 B2 | 7/2018 | Zhang et al. |
| 10,154,869 B2 | 12/2018 | Onik et al. |
| 10,154,876 B2 | 12/2018 | Callas et al. |
| 10,252,050 B2 | 4/2019 | Kreis et al. |
| 10,850,095 B2 | 12/2020 | Ebbers et al. |
| 10,857,347 B2 | 12/2020 | Danitz et al. |
| 2001/0025177 A1 | 9/2001 | Woloszko et al. |
| 2002/0120260 A1 | 8/2002 | Morris et al. |
| 2002/0193833 A1 | 12/2002 | Dimmer et al. |
| 2003/0204161 A1 | 10/2003 | Petric |
| 2003/0229316 A1 | 12/2003 | Hwang et al. |
| 2003/0233087 A1 | 12/2003 | Chen et al. |
| 2004/0080964 A1 | 4/2004 | Buchmann |
| 2004/0181237 A1 | 9/2004 | Forde et al. |
| 2004/0186466 A1 | 9/2004 | Chomenky et al. |
| 2004/0240241 A1 | 12/2004 | Chueh et al. |
| 2004/0267254 A1 | 12/2004 | Manzo et al. |
| 2005/0119627 A1 | 6/2005 | Crawford |
| 2005/0119649 A1 | 6/2005 | Swanson |
| 2005/0171534 A1 | 8/2005 | Habib |
| 2006/0015147 A1 | 1/2006 | Persson et al. |
| 2006/0062074 A1 | 3/2006 | Gundersen et al. |
| 2006/0079886 A1 | 4/2006 | Orszulak et al. |
| 2006/0090723 A1 | 5/2006 | Stuart |
| 2006/0139977 A1 | 6/2006 | Oicles et al. |
| 2007/0129626 A1 | 6/2007 | Mahesh et al. |
| 2008/0015516 A1 | 1/2008 | Lavi |
| 2008/0031337 A1 | 2/2008 | Hasegawa et al. |
| 2008/0077189 A1 | 3/2008 | Ostroff |
| 2008/0231337 A1 | 9/2008 | Krishnaswamy et al. |
| 2009/0012513 A1 | 1/2009 | Utley et al. |
| 2009/0198231 A1 | 8/2009 | Esser et al. |
| 2009/0247944 A1 | 10/2009 | Kirschenman et al. |
| 2009/0299362 A1 | 12/2009 | Long et al. |
| 2010/0038971 A1 | 2/2010 | Sanders et al. |
| 2010/0042095 A1 | 2/2010 | Bigley et al. |
| 2010/0049194 A1 | 2/2010 | Hart et al. |
| 2010/0063496 A1 | 3/2010 | Trovato et al. |
| 2010/0240995 A1 | 9/2010 | Nuccitelli et al. |
| 2010/0331758 A1 | 12/2010 | Davalos et al. |
| 2011/0015630 A1 | 1/2011 | Azure |
| 2011/0092973 A1 | 4/2011 | Nuccitelli et al. |
| 2011/0112527 A1 | 5/2011 | Hamilton et al. |
| 2011/0118729 A1 | 5/2011 | Heeren et al. |
| 2011/0144641 A1 | 6/2011 | Dimalanta et al. |
| 2011/0160514 A1 | 6/2011 | Long et al. |
| 2011/0264179 A1 | 10/2011 | Eckerdal |
| 2011/0270249 A1 | 11/2011 | Utley et al. |
| 2011/0319833 A1 | 12/2011 | Chun et al. |
| 2012/0109263 A1 | 5/2012 | Kolb et al. |
| 2012/0130269 A1* | 5/2012 | Rea ............ A61B 5/4893 607/42 |
| 2012/0136282 A1 | 5/2012 | Rosenberg et al. |
| 2012/0158078 A1 | 6/2012 | Moulder et al. |
| 2012/0277624 A1 | 11/2012 | Cucin |
| 2012/0277763 A1 | 11/2012 | Greenblatt et al. |
| 2012/0310230 A1 | 12/2012 | Willis |
| 2013/0018441 A1 | 1/2013 | Childs |
| 2013/0060246 A1 | 3/2013 | Knopp et al. |
| 2013/0190836 A1 | 7/2013 | McCreery |
| 2013/0289358 A1 | 10/2013 | Melsky et al. |
| 2013/0302409 A1 | 11/2013 | Fuchs et al. |
| 2013/0345697 A1 | 12/2013 | Garcia et al. |
| 2014/0005658 A1 | 1/2014 | Rosenbegr |
| 2014/0046322 A1 | 2/2014 | Callas et al. |
| 2014/0081256 A1 | 3/2014 | Carmel et al. |
| 2014/0155963 A1 | 6/2014 | Ko |
| 2014/0194789 A1 | 7/2014 | Ko |
| 2014/0200403 A1 | 7/2014 | West et al. |
| 2014/0228835 A1 | 8/2014 | Mielekamp et al. |
| 2014/0277219 A1 | 9/2014 | Nanda |
| 2014/0336638 A1 | 11/2014 | Deem et al. |
| 2014/0364797 A1 | 12/2014 | Schoenbach et al. |
| 2015/0032100 A1 | 1/2015 | Coulson et al. |

(56) References Cited

U.S. PATENT DOCUMENTS

| | | |
|---|---|---|
| 2015/0065946 A1 | 3/2015 | Gehl et al. |
| 2015/0201991 A1 | 7/2015 | Zemlin |
| 2015/0230855 A1 | 8/2015 | Chomenky et al. |
| 2015/0230858 A1 | 8/2015 | Long et al. |
| 2015/0272657 A1 | 10/2015 | Yates et al. |
| 2015/0318846 A1 | 11/2015 | Prager et al. |
| 2016/0192999 A1 | 7/2016 | Stulen et al. |
| 2016/0271380 A1 | 9/2016 | Poon et al. |
| 2016/0296269 A1 | 10/2016 | Rubinsky et al. |
| 2016/0317216 A1 | 11/2016 | Hermes et al. |
| 2016/0338761 A1 | 11/2016 | Chomenky et al. |
| 2016/0361109 A1 | 12/2016 | Weaver et al. |
| 2016/0367310 A1 | 12/2016 | Onik et al. |
| 2017/0127987 A1 | 5/2017 | Hezi-Yamit et al. |
| 2017/0209695 A1 | 7/2017 | Solomon |
| 2017/0216353 A1* | 8/2017 | Nuccitelli ............ G01N 33/574 |
| 2017/0245928 A1 | 8/2017 | Xiao et al. |
| 2017/0246455 A1 | 8/2017 | Athos et al. |
| 2017/0281274 A1 | 10/2017 | Santana |
| 2017/0319851 A1 | 11/2017 | Athos et al. |
| 2017/0348525 A1 | 12/2017 | Sano et al. |
| 2018/0078755 A1 | 3/2018 | Kreis et al. |
| 2018/0110557 A1 | 4/2018 | Muratori et al. |
| 2018/0154141 A1 | 6/2018 | Ahn |
| 2018/0154142 A1 | 6/2018 | Guo et al. |
| 2018/0177543 A1 | 6/2018 | You et al. |
| 2018/0243558 A1 | 8/2018 | Athos et al. |
| 2019/0009084 A1 | 1/2019 | Stadelmann et al. |
| 2019/0046791 A1* | 2/2019 | Ebbers ................. A61N 1/0476 |
| 2019/0109591 A1 | 4/2019 | Miller et al. |
| 2019/0217080 A1 | 7/2019 | Moss et al. |
| 2019/0269904 A1 | 9/2019 | Kreis et al. |
| 2020/0261720 A1 | 8/2020 | Danitz et al. |
| 2021/0085958 A1 | 3/2021 | Danitz et al. |
| 2023/0248415 A1 | 8/2023 | Danitz et al. |

FOREIGN PATENT DOCUMENTS

| | | |
|---|---|---|
| WO | WO03/076006 A2 | 9/2003 |
| WO | WO2011/146498 A2 | 11/2011 |
| WO | WO2011/163264 A2 | 12/2011 |
| WO | WO2013/143603 A1 | 10/2013 |
| WO | WO2014/060854 A1 | 4/2014 |
| WO | WO2016/089781 A1 | 6/2016 |
| WO | WO2017/200954 A1 | 11/2017 |
| WO | WO2017/201394 A1 | 11/2017 |
| WO | WO2017/223120 A1 | 12/2017 |
| WO | WO2018/075946 A1 | 4/2018 |
| WO | WO2018/089506 A1 | 5/2018 |
| WO | WO2018/106672 A1 | 6/2018 |

OTHER PUBLICATIONS

Extended European Search Report mailed Feb. 11, 2022 for European Patent Application 19741574.8; 8 pages.

Anand et al.; Adaptive immune response to nano-pulse stimulation (NPS); Nov. 11, 2016, Poster presentation at the 31st Annual Meeting and Associated Programs of the Society for Immunotherapy of Cancer; 1 page; retreived rom the internet (http://pulsebiosciences.com/assets/Pulse%20AIR%20poster.pdf); on Mar. 13, 2018.

Baker et al.; Stacking power Mosfets for use in high speed instrumentation; Review of scientific instruments; 63(12; pp. 5799-5801; Dec. 1992.

Beebe; Hepatocellular carcinoma ablation and possible immunity in the age of nanosecond pulsed electric fields; Journal of Hepatocellular carcinoma; No. 2; pp. 49-55; May 2015.

Bhosale et al.; Design and Simulation of 50 kV, 50 A Solid State Marx Generator; International Conference on Magnetics, Machines & Drives (AICERA—2014 iGMMD), IEEE; pp. 1-5; Jul. 24, 2014.

Carey et al.; Marx Generator Design and Performance; IEEE; InPower Modulator Symposium, 2002 High-Voltage Workshop; Conference Record of the Twenty-Fifth International; Applied Physical Electronics, Austin TX; 4 pages; Jun. 2002.

Casey et al.; Solid-State Marx Bank Modulator for the Next Generation Linear Collider; Conference Record of the 26th; IEEE; International Power Modulator Symposium and 2004 High Voltage Workshop (PMC), San Francisco, California; pp. 257-260; May 23-26, 2004.

Cook et.al.; Design and Testing of a Fast, 50 kV Solid-State Kicker Puiser; IEEE; Inconference record of the International Power Modulator Symposium 2002; pp. 106-109; Lawrence Livermore National lab; 6 pages; Jun. 24, 2002.

Garon et al.; In Vitro and In Vivo Evaluation and a Case Report of Intense Nanosecond Pulsed Electric Field as a Local Therapy for Human Malignancies; International Journal of Cancer; 121(3); pp. 675-682; Aug. 2007.

Gaudreau et al; Solid-State Pulsed Power Systems for the Next Linear Collider; IEEE; InPulsed Power Plasma Science, 2001, PPPS-2001. Digest of Technical Papers; vol. 1; pp. 298-301; Jun. 17, 2001.

Gundersen et al.; Nanosecond pulse generator using a fast recovery diode; IEEE; InProceedings of the 26th Inernational Pulsed Modulator Conference; 603-606; (year of pub. sufficiently earlier than effective US filing date and any foreign priority date) 2004.

Jiang et al.; Marx Generator Using Power Mosfets; IEEE; InPulsed Power Conference, PPC/09; pp. 408-410; Jun. 28, 2009.

Kirbie et al.; An All Solid State Pulse Power Source for High PRF induction Accesierators; InPower Modulator Symposium, 1988; Conference Rceord of the 1988 Twenty-Third International, Rancho Mirage, Ca.; ; pp. 6-11; 6 pages; Jun. 22-25, 1998.

Krasnykh et al.; A Solid State Marx Type Modulator for Driving a TWT; Conference Record of the 24th International Power Modulator Sypolsium 2000; pp. 209-211; Jun. 26, 2000.

McDaniel et al., Nanosecond pulsed electric field treatment of tumor cell lines triggers immunogenic cell death (ICD); Nov. 11, 2016, Poster presentation at the 31st Annual Meeting and Associated Programs of the Society for Immunotherapy of Cancer (SITC 2016), National Harbor, MD, USA; 1 page; retrieved from the Internet (http://pulsebiosciences.com/assets/Pulse%20ICD%20poster.pdf) on Mar. 13, 2018.

Okamura et al.; Development of the High Repetitive impulse Voltage Generator Using Semiconductor Switches; IEEE; InPulsed Power Conference; Digest of Technical Papers, 12 th IEEE International; vol. 2; pp. 807-810; Jun. 27, 1999.

Redondo et al.; Solid-State Marx Generator Design with an Energy Recovery ReseS Circuit for Output Transformer Association; InPower Electronics Spelalists Conference, 2007, PESC, IEEE 2007; pp. 2987-2992; (5 pages); Jun. 17, 2007.

Richter-Sand et al.; Marx-Stacked IGBT Modulators for High Voltage. High Power Applications; IEEE; InPower Modulator Symposium, 2002 and 2002 High-Voltage Workshop., Conference Record of the Twenty-Fifth International 2002; pp. 390-393; Jun. 30, 2002.

Sack et al.; Design Considerations for a Fast Stacked-MOSFET Switch; IEEE Transactions on Plasma Science; 41(10); pp. 2630-2636; Oct. 2013.

Tang et al.; Diode Opening Switch Based Nanosecond High Voltage Pulse Generators for Biological and Medical Applications; IEEE Transactions on Dielectrics and Electrical Insulation; 14(4); pp. 878-883; Aug. 2007.

Wang et al.; Solid-State High Voltage Nanosecond Pulse Generator; IEEE InPulsed Power Conference;pp. 1199-1202; 4 pages; Jun. 13, 2005.

Yao et al.; FPGA-Controlled All-Solid-State Nanosecond Pulse Generator for Biological Applications; IEEE Transactions on Plasma Science; 40(10; pp. 2366-2372; Oct. 2012.

Yatim et al.; RIPK1 and NF-xB signaling in dying cells determines cross-priming of CD8+T cells; Science; 350(6258); pp. 328-334; Oct. 16, 2015.

International Search Report and Written Opinion mailed Jan. 8, 2018 for PCT/US2017/05340; 10 pages.

International Search Report and Written Opinion mailed Apr. 21, 2016 for PCT/US2015/63025; 9 pages.

International Search Report and Written Opinion mailed Jul. 21, 2017 for PCT/US2017/032744; 11 pages.

International Search Report and Written Opinion mailed Feb. 27, 2018 for PCT/US2017/060654; 18 pages.

(56) References Cited

OTHER PUBLICATIONS

International Search Report and Written Opinion mailed Apr. 21, 2017 for PCT/US2017/015884; 12 pages.
International Search Report and Written Opinion mailed May 25, 2017 for PCT/US2017/015881; 13 pages.
International Search Report and Written Opinion mailed Dec. 11, 2018 for PCT/US2018/045433; 16 pages.
Invitation to Pay Additional Fees and, Where Applicable, Protest Fee mailed Mar. 15, 2017 for PCT/US2017/015881; 2 pages.
International Search Report and Written Opinion mailed May 1, 2019 for PCT/US2019/013545; 10 pages.
International Search Report and Written Opinion mailed Apr. 29, 2019 for PCT/US2019/013484; 21 pages.
International Search Report mailed Feb. 27, 2018 for PCT/US2017/057698; 5 pages.
International Search Report mailed Mar. 22, 2018 for PCT/US2017/064685; 6 pages.
International Search Report mailed May 22, 2018 for PCT/US2018/019213; 4 pages.
Preliminary Report on Patentability mailed Mar. 19, 2019 for PCT/US2017/052340; 6 pages.
Final Office action mailed Jul. 5, 2019 for U.S. Appl. No. 15/269,273; 12 pages.
Non Final Office Action mailed Dec. 26, 2018 for U.S. Appl. No. 15/269,273; 8 pages.
McDaniel et al.; P329 Nanosecond pulsed electric field treatment of tumor cell lines triggers immunogenic cell death (ICD); Journal for Immuno Therapy of Cancer: 31st Annual Meeting and Associated Programs of the Society for Immunotherapy of Cancer (SITC 2016): part two: National Harbor, MD, USA, p. 175; Nov. 16, 2016.
Anand et al., "Nano-Pulse Electro-Signaling treatment of murine tumors significantly reduces the percentage of regulatory T cells in the treated tumor," Journal for Immunotherapy of Cancer: 31 st Annual Meeting and Associated Programs of the Society for Immunotherapy of Cancer (SITC 2016), Part Two, National Harbor, MD, USA; p. 214; Nov. 16, 2016.

* cited by examiner

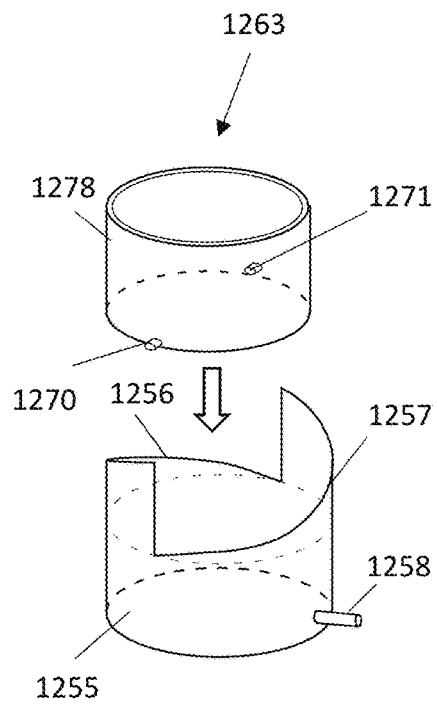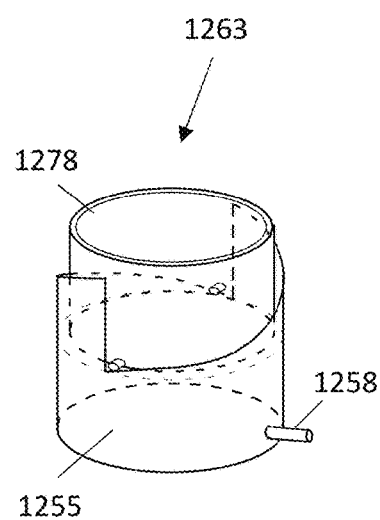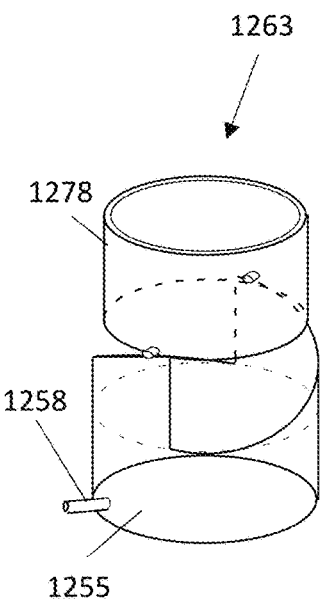
FIG. 12C  FIG. 12D  FIG. 12E
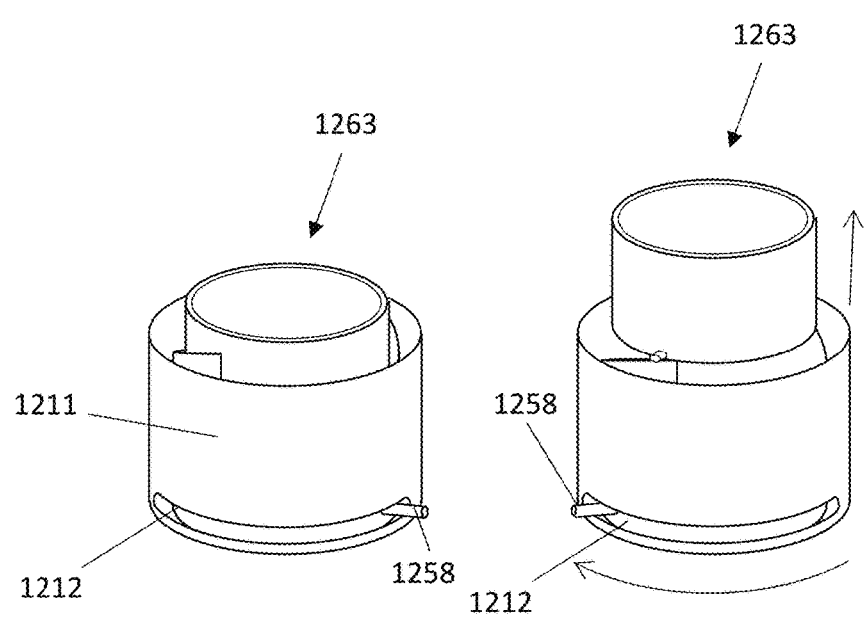
FIG. 12F  FIG. 12G

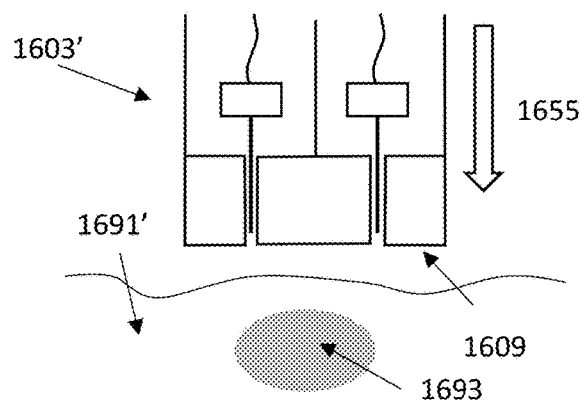
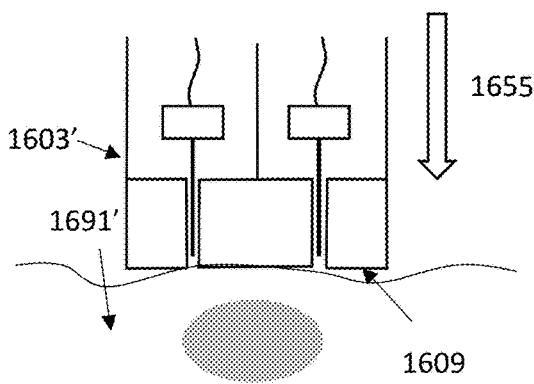
FIG. 16G
FIG. 16H
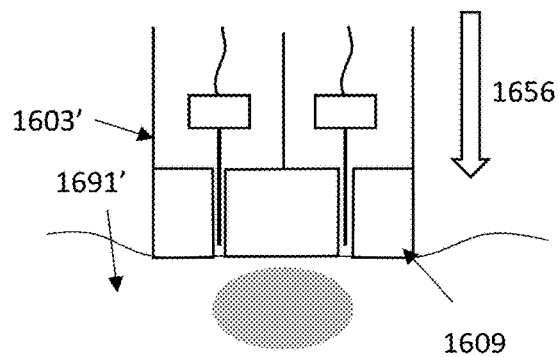
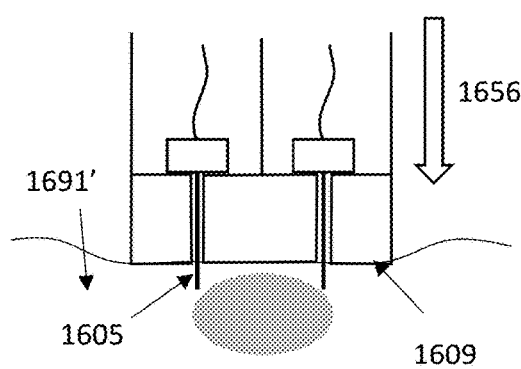
FIG. 16I
FIG. 16J
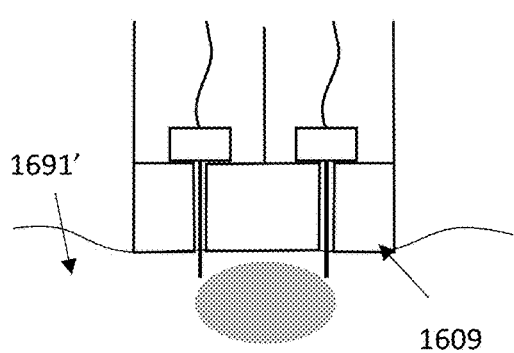
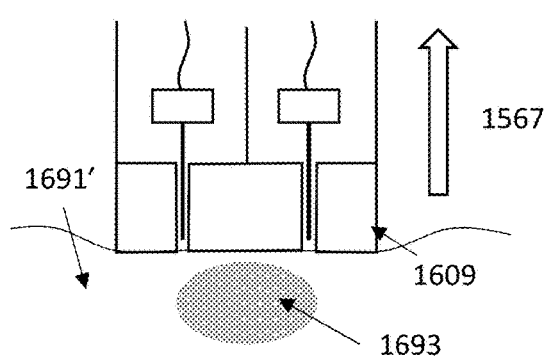
FIG. 16K
FIG. 16L

METHODS OF TREATMENT USING TREATMENT APPLICATOR WITH PROTECTED ELECTRODES

CROSS REFERENCE TO RELATED APPLICATIONS

This application is a continuation of U.S. patent application Ser. No. 16/247,469, filed Jan. 14, 2019, titled "TREATMENT TIP WITH PROTECTED ELECTRODES", now U.S. Pat. No. 11,167,125, which application claims the benefit of priority to U.S. Provisional Patent Application No. 62/618,022, filed Jan. 16, 2018, titled "TREATMENT TIP WITH PROTECTED NEEDLES", both of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are electrical applicators that may be preferentially used to apply high voltage, ultra-short electrical pulses to treat patients. Specifically, described herein are retractable treatment tip apparatuses and methods of using them for high-voltage nanosecond pulse electrical therapy.

BACKGROUND

Ultra-short, high-field strength electric pulses have been described for electroperturbation of biological cells. For example, electric pulses may be used in treatment of human cells and tissue including tumor cells, such as basal cell carcinoma, squamous cell carcinoma, and melanoma. The voltage induced across a cell membrane may depend on the pulse length and pulse amplitude. Pulses longer than about 1 microsecond may charge the outer cell membrane and lead to opening of pores, either temporarily or permanently. Permanent openings may result in instant or near instant cell death. Pulses shorter than about 1 microsecond may affect the cell interior without adversely or permanently affecting the outer cell membrane, and result in a delayed cell death with intact cell membranes. Such shorter pulses with a field strength varying in the range of 10 kV/cm to 100 kV/cm may trigger apoptosis (i.e., programmed cell death) in some or all of the cells exposed to the described field strength and pulse duration. These higher electric field strengths and shorter electric pulses may be useful in manipulating intracellular structures, such as nuclei and mitochondria.

Nanosecond high voltage pulse generators have been proposed for biological and medical applications. For example, see: Gundersen et al. "Nanosecond Pulse Generator Using a Fast Recovery Diode", IEEE 26th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Yampolsky et al., "Repetitive Power Pulse Generator With Fast Rising Pulse" U.S. Pat. No. 6,831,377; Schoenbach et al. "Method and Apparatus for Intracellular Electro-Manipulation", U.S. Pat. No. 6,326,177; Gundersen et al., "Method for Intracellular Modifications Within Living Cells Using Pulsed Electric Fields", U.S. Patent Application No. 2006/0062074; Kuthi et al., "High Voltage Nanosecond Pulse Generator Using Fast Recovery Diodes for Cell Electro-Manipulation", U.S. Pat. No. 7,767,433; Krishnaswamy et al., "Compact Sub-nanosecond High Voltage Pulse Generation System for Cell Electro-Manipulation", U.S. Patent Application No. 2008/0231337; and Sanders et al., "Nanosecond Pulse Generator", U.S. Patent Application No. 2010/0038971. The entire content of these publications is incorporated herein by reference.

Because of the extremely high therapeutic voltages, as well as the very fast pulse times, applicators for delivery of such nanopulse stimulation devices must be configured so as to avoid arcing between the applicators. In some cases, the applicator may be configured to penetrate into the tissue for application, and may include multiple needle-type electrodes. Such applicators may be particularly difficult to use with high-voltage systems while avoiding dangerous arcing. In some variations, the applicator may require the use of an nonconductive material, such as a non-conductive gel, between the patient's tissue and the applicator. The methods and apparatuses described and illustrated herein may address the issues discussed above.

SUMMARY OF THE DISCLOSURE

Described herein are apparatuses (e.g., devices and systems, including treatment tip applicators) and methods for the treatment of tissue that may more effectively apply therapeutic energy, including but not limited to ultra-short, high field strength electric pulses, while avoiding the risk of arcing or otherwise harming the tissue. These applicators may be particularly well suited, for example, for treatments of various diseases, skin disorders, and abnormal tissue growth.

In particular, the apparatuses described herein may be configured as single-use treatment tips that can be used with a variety of different reusable generator systems, as will be described in greater detail herein.

The methods and apparatuses described herein include treatment tips having a portion of the distal tip region that may be retracted. Any of these apparatuses may include an electrode partition, which may be configured as a housing, to protect and/or insulate a plurality of treatment electrodes through which high-voltage rapidly pulsed energy may be delivered into the tissue. These apparatuses may address various issues with existing treatment tips. In particular, these apparatuses may be configured safely and reliably to deliver nanopulse electric treatment. Nanopulse electric treatment may be referred to as nanosecond pulsed electric field (nsPEF) stimulation and may include an electric field with a sub-microsecond pulse width of between 0.1 nanoseconds (ns) and 1000 nanoseconds, or shorter, such as 1 picosecond. It is sometimes referred to as sub-microsecond pulsed electric field. NsPEFs often have high peak voltages, such as 10 kilovolts per centimeter (kV/cm), 20 kV/cm, to 500 kV/cm. Treatment of biological cells with nsPEF technology often uses a multitude of periodic pulses at a frequency ranging from 0.1 per second (Hz) to 10,000 Hz. NsPEFs have been found to trigger apoptosis, for example, in the diseased tissue or abnormal growth, such as cancerous or benign tumors. Selective treatment of such tumors with nsPEFs can induce apoptosis within the tumor cells without substantially affecting normal cells in the surrounding tissue due to its non-thermal nature. An example of nsPEF applied to biological cells is shown and described in U.S. Pat. No. 6,326,177 (to Schoenbach et al.), which is incorporated herein by reference in its entirety for all purposes. There exists a need for electrodes to deliver nsPEF pulses generated by a pulse generator to subjects with minimal distortion and with maximum utility and safety. A subject may be a patient (human or non-human, including animals). A user may operate the apparatuses described herein on a subject. The user may be a physician (doctor, surgeon, etc.), medical technician, nurse, or care provider.

For example, described herein are treatment tip devices for delivery of electrical therapy. Any of the treatment tip devices described herein may include: a treatment tip housing; an electrode partition extending from a distal end of the treatment tip housing, wherein the electrode partition is configured to retract proximally into the treatment tip housing; and a plurality of treatment electrodes, comprising a first electrode and a second electrode, wherein a distal tip of the first electrodes and a distal tip of the second electrode are exposed distally beyond the electrode partition in a deployed configuration when the electrode partition is driven against a subject's tissue, wherein the distal tip of the first electrode is separated from the distal tip of the second electrode by the electrode partition in an un-deployed configuration prior to driving the electrode partition against the subject's tissue.

As mentioned, the electrode partition may be configured to partially or completely cover all or some of the plurality of electrodes when in the un-deployed state. The electrode partition may therefore be referred to herein as an electrode housing; in some variations the electrode partition does not enclose the electrodes but separates (e.g., partitions) electrodes in the plurality of electrodes from each other, including electrically isolating them, particularly when applied against a tissue. This may prevent or reduce arcing, and may prevent accident injury, and/or may guide the electrodes, particularly needle electrodes, during insertion into the tissue.

Thus, unless the context makes it clear otherwise, any of the electrode partitions described herein may be referred to as an electrode housing, and an electrode housing may refer to an electrode partition that at least partially encloses all or some of the electrodes of the plurality of electrodes. For example, an electrode partition may comprise an electrode housing and the plurality of treatment electrodes may at least partially be housed within the electrode partition when the device is in the un-deployed configuration. Either the electrode partition or the electrode housing may include lateral openings that expose at least part of the one or more electrodes of the plurality of electrodes.

For example, the electrode housing may comprise one or more lateral cut-out regions (e.g., openings, windows, etc.) configured so that at least part of a lateral side of one or more of the electrodes from the plurality of electrodes are visible in the un-deployed configuration.

As mentioned, in some variations, the treatment tip includes an electrode partition configured as an electrode housing. The electrode housing may completely enclose all or some of the plurality of electrodes in the un-deployed configuration, or it may partially enclose all or some of the plurality of electrodes in the un-deployed configuration (e.g., the electrode housing may be open at the distal end face and/or open along one or more, or part of one or more, sides.

According to some implementations, a treatment tip device for delivery of electrical therapy may include: a treatment tip housing; an electrode housing extending from a distal end of the treatment tip housing; and a plurality of treatment electrodes at least partially within the electrode housing, wherein the device has an un-deployed configuration in which distal ends of the plurality of treatment electrodes do not extend beyond a distal end face of the electrode housing and a deployed configuration in which the plurality of treatment electrodes extend beyond the distal end face of the electrode housing, wherein the electrode housing and treatment electrodes are configured to move relative to each other to convert between the un-deployed and the deployed configurations.

According to further implementations, for example, a treatment tip device for delivery of electrical therapy comprises: a treatment tip housing; an electrode housing extending from a distal end of the treatment tip housing and configured to retract proximally into the treatment tip housing; a plurality of treatment electrodes at least partially within the electrode housing, wherein the device has an un-deployed configuration in which distal ends of the plurality of treatment electrodes do not extend beyond a distal end face of the electrode housing and a deployed configuration in which the electrode housing is retracted proximally so that the distal ends of the plurality of treatment electrodes extend beyond the distal end face of the electrode housing; and a bias opposing retracting the electrode housing from the un-deployed configuration to the deployed configuration.

It is further provided a treatment tip device for delivery of electrical therapy, the device comprising: a treatment tip housing having a plurality of electrical connectors; an electrode housing extending from a distal end of the treatment tip housing, wherein a distal end face of the electrode housing comprises a soft and electrically insulating material and wherein the electrode housing is configured to retract proximally into the treatment tip housing in a deployed configuration; a plurality of treatment electrodes comprising a first needle electrode and a second needle electrode wherein a distal end of the first needle electrode is separated from a distal end of the second needle electrode by the electrode housing in an un-deployed configuration, further wherein the plurality of treatment electrodes is in electrical communication with the plurality of electrical connectors; wherein the device converts between the un-deployed configuration, in which the distal ends of the plurality of treatment electrodes do not extend beyond a distal end face of the electrode housing, and the deployed configuration in which the electrode housing is retracted proximally so that the distal ends of the plurality of treatment electrodes extend beyond the distal end face of the electrode housing.

Any of the treatment tip devices described herein may include a bias that prevents or limits the conversion between the un-deployed and deployed configuration. As used herein, a bias generally includes any mechanical resistance element that my limit or prevent the movement of the electrode partition or electrode housing relative to the plurality of electrodes, typically from an un-deployed to a deployed configuration, until an appropriate threshold force is applied. In some variation the bias may provide a return force (e.g., spring force or bias force) tending to return the electrode partition or electrode housing back to the un-deployed configuration. In some variations the bias may be a release element that prevents movement of the electrode partition or electrode housing relative to the plurality of electrodes until the threshold is exceeded, after which the release disengages, allowing deployment from the un-deployed configuration. For example, a bias may comprise one or more of the following: a mechanical resistor, a spring, a detent, a catch, a piston, a mechanical dampener, a compressible material, a release, a friction release, a deflectable release, frangible release, and a frictional coupling. The threshold force may be any appropriate threshold force and may typically be low enough to permit a user to, by hand, deploy the device by manually pushing against the tissue. For example, the threshold force may be between 0.01 pounds and 10 pounds of force, e.g., the threshold may be 0.01 pounds of force, 0.03 pounds of force, 0.05 pounds of force, 0.07 pounds of force, 0.1 pounds of force, 0.12 pounds of force, 0.15 pounds of force, 0.2 pounds of force, 0.3 pounds of force, 0.5 pounds of force, 1 pound of force, 1.5 pounds of force, 2 pounds of force, 5 pounds of force, etc.). In general, any appropriate bias may be used, e.g., to bias the electrode partition in the un-deployed configuration. As mentioned, the bias may be a mechanical bias, such as a spring (e.g., coil spring, leaf spring, etc.), an electrical or electromagnetic bias (e.g., a solenoid, etc.), a pneumatic bias, or the like. The bias may be within the treatment tip housing and/or within the electrode partition. The bias may apply force between the treatment tip housing and the electrode partition; in some variations the bias may instead or in addition apply force between the treatment tip housing and the plurality of therapeutic electrodes.

Thus, any of the devices described herein may include a bias exerting a bias force to oppose conversion from the un-deployed to the deployed configuration or from the deployed to un-deployed configuration. The bias may be overcome by applying a force of greater than the threshold force. The bias may be coupled or part of the treatment tip housing, the electrode partition (e.g., electrode housing), and/or the plurality of electrodes.

The bias may be configured to return the electrode housing distally to the un-deployed configuration with a bias return force. For example, the plurality of treatment electrodes may be extended distally from the electrode housing when the electrode housing is driven against a subject's tissue with a force exceeding threshold force (which, in variations having a return as part of the bias may be equivalent to the bias return force). The bias may be configured to drive the plurality of treatment electrodes distally with a bias force. In some variations the bias may include a release lock preventing the electrode partition (e.g., electrode housing) from driving the plurality of treatment electrodes distally until the release lock is released.

In general, a treatment electrode may be any appropriate number and/or groups of electrodes. For example, the plurality of treatment electrodes may comprise a first one or more treatment electrodes and a second one or more treatment electrodes separated from each other by the electrode housing. In some variations groups (subsets) of electrodes are grouped together and, though separately contacting the skin, may be linked electrically to the same source (e.g., anode, cathode, ground, etc.).

As mentioned above, the electrode housing may comprise at least one lateral cut-out (e.g., window) and the first one or more treatment electrodes may be positioned to be at least partially visible through the at least one lateral cut out. For example, at least one cut-out may extend along a portion of the length or the full length of the electrode housing.

All or a portion (e.g., the distal end) of the electrode partition may include an electrical insulator. This electrical insulator may be integral to the electrode partition distal end (e.g., distal-facing end or tissue-facing end), or it may be a cover or sleeve. For example, the electrode partition may be formed at least in part of the insulating material, or the insulating material may be added to other material forming the electrode partition. The electrode partition may also be referred to herein as a needle housing or a needle electrode partition.

In general, the electrical insulator may comprise a soft, insulating material having a durometer of 60 or less on the Shore A hardness scale. For example, the electrical insulator may comprise one or more of: silicon, santoprene, or other TPE (Thermoplastic Elastomer) materials. In any of the apparatuses (e.g., treatment tip devices) described herein may include a soft and/or insulated distal end face region of the electrode partition or electrode housing. For example, at least the distal end of the electrode housing comprises an electrical insulator. The electrical insulator may comprise a soft, insulating material having a durometer of 60 or less on the Shore A hardness scale. The electrical insulator comprises one or more of: silicon, santoprene, or other TPE (Thermoplastic Elastomer) materials. In some variations, the electrical insulator comprises an electrically insulating cover.

Any of these apparatuses may include one or more vacuum ports on the distal end (e.g., through the distal electrically insulating cover). The vacuum ports may apply suction to hold the distal electrically insulating end against the tissue when applying the treatment. The vacuum ports may couple to one or more vacuum lines within the treatment tip housing and/or electrode partition and may couple to a vacuum line (e.g., through the reusable handle). In any of the apparatuses described herein, the handle may be referred to as a headpiece. For example, any of these devices may include a vacuum port through the electrode housing (e.g., through the electrically insulating cover).

In general, the electrode partition (e.g., electrode housing) is configured to retract and extend into the treatment tip housing. However, in some variations, the plurality of treatment electrodes may be configured to retract and extend into the electrode housing.

In any of the apparatuses described herein, the treatment tip housing may include a proximal coupling region configured to couple to an applicator and wherein the proximal coupling region of the treatment tip housing comprises a plurality of electrical connectors that are in electrical communication with the plurality of treatment electrodes. Also, in any of the devices described herein, the distal-to-proximal length of the plurality of treatment electrodes may be adjustable.

In general, although the electrodes described herein are shown primarily as needle electrodes, it should be understood that any of these electrodes may be any other type of electrode, such as, e.g., plate electrodes, probe electrodes, knife electrodes, or the like. The electrodes may be configured to penetrate tissue (e.g., having a sharp, pointed, beveled, or otherwise cutting or penetrating end or edge) or they may be non-penetrating electrodes (e.g., rounded, etc.). As mentioned, any of the treatment electrodes may comprise treatment needle electrodes. Needle electrodes may include elongate metal electrodes that may have pointed, tissue-penetrating distal ends. In any of these variations, the electrode housing may include a needle guide configured to guide the needle electrodes. Needle guides may be channels that hold the needle in an orientation (e.g., perpendicular to the distal face of the electrode housing) and may help keep the electrode(s) from bending or curving as they enter the tissue, e.g., as the electrode housing is retracted. An electrode housing including or configured as a needle guide may include one or more openings (channels) that prevent the needle from bending or curving as it enters the tissue. For example, an electrode housing may include a tube or channel having an inner diameter that is approximately the same dimensions (or slightly larger) than the outer dimension of the needle electrodes, allowing it to pass through the channel, perpendicular to the face of the electrode housing, and into the tissue without bending or curving. For example, a needle guide may be within the electrode housing/partition and configured to guide the plurality of treatment electrodes as the electrode partition is deployed when the electrode partition is driven against a subject's tissue. Thus, any of the apparatuses described herein may include a guide (e.g., electrode guide or needle guide) within and/or adjacent to the electrode partition that is configured to guide the electrodes as the electrode partition extends and retracts over them and into/out of the treatment tip housing. For example, the electrode guide (or multiple electrode guides may provide a channel or passage that prevents the electrode from bending or curving when inserting into the tissue. This may be particularly helpful with long treatment needle electrodes. A guide (e.g., needle guide) may be a cylinder or other shaped channel through which the electrodes pass when the electrode partition is retracted or extended over the treatment electrodes.

Any of the devices described herein may include one or more fiducial marker on the electrode partition (e.g., electrode housing) and/or a cover for an electrode housing. The fiducial maker may include one or more fiducial line on the electrode housing. The fiducial marker may include one or more fiducial lines in alignment with one or more rows of treatment electrodes of the plurality of treatment electrodes, wherein the fiducial lines identify a location and orientation of the one or more rows of the plurality of treatment electrodes (e.g., within the housing in the un-deployed configuration). For example, any of these apparatus may include one or more fiducial markers or markings on the outer surface of the retractable electrode partition. For example, the apparatus may include a fiducial line (or a plurality of lines) on the electrode partition. These markings may be labeled (e.g., with alphanumeric characters and/or colors and/or patterns). Fiducial markings may be aligned with the therapeutic electrodes (e.g., rows of needle electrodes) to help the users align and place the treatment tip in the proper location on the lesion or treatment area.

Any of the devices described herein may include a stop limiting a proximal distance that the electrode housing/partition may be driven in the deployed configuration. The stop may be adjustable to change the distance that the electrode housing/partition may be driven in the deployed configuration. The stop may be, for example, a mechanical stop within the tip housing that limits the proximal distance that the electrode partition may be driven (retracted) when applying the force exceeding the threshold force that may be set by the bias (e.g., in some variations may be equivalent to a bias return force). The mechanical stop may include a rim, ridge, or boss, and may be within the housing. The stop may be adjustable (e.g., using a control on the treatment tip housing and/or handle). The stop may be adjustable to change the proximal distance that the electrode partition may be driven when applying the force exceeding the threshold force.

Also described herein are insulating covers for a needle electrodes (including any of the needle electrodes described above). The insulating cover may include: a soft body configured to fit over a distal end of a housing for a needle electrode, wherein the soft body comprises an electrically insulating material having a durometer of 60 or less on the Shore A hardness scale; and a channel through the soft body configured to pass the needle electrode.

The soft body may comprise a raised ring around the channel. In some variations, the raised ring forms a gasket. The soft body may comprise a durometer of 45 or less. Any of these insulting covers may include a plurality of channels through the soft body.

As mentioned above, a treatment tip device for delivery of electrical therapy may include: a treatment tip housing; an electrode partition extending from a distal end of the treatment tip housing; a plurality of treatment electrodes comprising a first one or more treatment electrodes and a second one or more treatment electrodes, wherein the device has an un-deployed configuration in which the distal ends of the first one or more treatment electrodes are separated from the distal ends of the second one or more treatment electrodes by the electrode partition, and a deployed configuration in which the plurality of treatment electrodes extend distally beyond the electrode partition, further wherein the electrode partition and treatment electrodes are configured to move relative to each other to convert between the un-deployed and the deployed configurations; and a bias within the treatment tip housing exerting a force to oppose conversion from the un-deployed to the deployed configuration or from the deployed to un-deployed configuration.

Any of the retractable treatment tip devices for delivery of electrical therapy may include: a treatment tip housing; an electrode partition extending from a distal end of the treatment tip housing, wherein the electrode partition is configured to retract proximally into the treatment tip housing; a bias driving the electrode partition distally with a bias return force; and a plurality of treatment electrodes, comprising a first electrode and a second electrode, wherein a distal tip of the first electrodes and a distal tip of the second electrode are exposed distally beyond the electrode partition when the electrode partition is driven against a subject's tissue with a force exceeding the threshold force to overcome the bias, and wherein otherwise the distal tip of the first electrode is separated from the distal tip of the second electrode by the electrode partition.

For example, a retractable treatment tip device for delivery of electrical therapy may include: a treatment tip housing; an electrode partition extending from a distal end of the treatment tip housing, wherein the electrode partition is configured to retract proximally into the treatment tip housing, further wherein a distal end face of the electrode partition comprises an electrical insulator; a bias holding and/or driving the electrode partition distally with a bias return force; and a plurality of treatment electrodes within the electrode partition; and wherein the plurality of treatment electrodes is exposed beyond the electrical insulator when the electrode partition is driven against a subject's tissue with a force exceeding a threshold force sufficient to overcome the bias.

In some variations, a retractable treatment tip device for delivery of electrical therapy includes: a treatment tip housing having a proximal coupling region comprising a plurality of electrical connectors; an electrode partition extending from a distal end of the treatment tip housing, wherein the electrode partition is configured to retract proximally into the treatment tip housing; a plurality of treatment needle electrodes comprising a first electrodes and a second electrode wherein the first electrode is separated from the second electrode by the electrode partition, further wherein the plurality of treatment needle electrodes are in electrical communication with the plurality of electrical connectors; and a bias within the treatment tip housing holding or driving the electrode partition distally with a bias return force so that a distal tip of the first electrode is separated from a distal tip of the second electrode by the electrode partition; a distal electrically insulating cover on a distal end of the electrode partition, wherein the distal electrically insulating cover comprises a soft material, further wherein the plurality of treatment needle electrodes extend distally beyond the distal electrically insulating cover when the electrode partition is driven against a subject's tissue with a force exceeding the threshold force so that the electrode partition is driven proximally relative to the plurality of treatment needle electrodes.

The treatment tip housing may be configured as a rigid, semi-rigid and/or semi-compliant region into which the electrode partition and/or electrodes may be at least partially retracted. The treatment tip housing may be configured to electrically connect the one or more electrodes with a controller and/or power source. Any of the treatment tip housings described herein may be configured as a handle or may connect to a handle. The treatment tip housing may be made of, e.g., a polymeric material (e.g., plastic) and may be sterilized. The device, including the treatment tip housing, may be reusable, multiple-use and/or disposable.

In some variations, the electrode partition may be configured as a housing that at least partially encloses the treatment electrodes. For example, described herein are treatment tip devices for delivery of electrical therapy (e.g., high-voltage nanosecond pulse electrical therapy) that include: a treatment tip housing; an electrode partition extending from a distal end of the treatment tip housing; a plurality of treatment needle electrodes within the electrode partition, wherein the device has an un-deployed configuration in which the distal ends of the treatment needle electrodes are within the electrode partition and a deployed configuration in which the plurality of treatment needle electrodes extend through the electrode partition, further wherein the electrode partition and treatment needle electrodes are configured to move relative to each other to convert between the un-deployed and the deployed configurations; and a bias within the treatment tip housing opposing conversion from the un-deployed to the deployed configuration until a force exceeding a threshold force is applied.

In some examples the plurality of treatment electrodes (e.g., treatment needle electrodes, or electrode plates, etc.) is configured to retract and extend into the treatment tip housing and/or the electrode partition. For example, the bias may be configured to drive the plurality of treatment electrodes distally once a force greater than a threshold force (e.g., greater than a bias return force when the bias is a spring) is applied. In some variations, the device may further comprise a release lock preventing the bias from driving the plurality of treatment electrodes distally until the release lock is released.

Alternatively or in addition, the electrode partition may be configured to retract and extend into the treatment tip at least partially (e.g., by at least 10%, by at least 20%, by at least 30%, by at least 40%, by at least 50%, by at least 60%, by at least 70%, by at least 80%, by at least 90%, by 100% of the extended length of the electrode partition,) within the treatment tip housing. For example, the bias (or a second bias) may be configured to drive the electrode partition distally with a bias return force, wherein the plurality of treatment electrodes is exposed distal to the electrode partition when the electrode partition is driven against a subject's tissue with a force exceeding the threshold force (which may be set by any included bias). In some variations, the electrode may be driven through and/or out of the electrode partition.

For example, described herein are retractable treatment tip devices for delivery of electrical therapy (e.g., high-voltage nanosecond pulse electrical therapy). The treatment tips described herein may also be referred to as applicators, applicator tips, retractable tips, or the like.

Any of these apparatuses may include, for example: a treatment tip housing; an electrode partition extending from a distal end of the treatment tip housing, wherein the electrode partition is configured to retract proximally into the treatment tip housing; a bias holding or in some variations driving the electrode partition distally until an applied force exceed a threshold; a plurality of treatment needle electrodes within the electrode partition; the disal end of the electrode partition may be electrically insulating, wherein the plurality of treatment needle electrodes is exposed through the distal electrically insulating end when the electrode partition is driven against a subject's tissue with a force exceeding the threshold force. As mentioned, this distal electrically insulating region may be an insulating cover or sleeve.

As mentioned, the treatment tip housing may be formed of a rigid, polymeric or other material and may be configured as a unitary (e.g., single piece) body, or it may be formed of multiple parts, e.g., segments, etc.) coupled together. The treatment tip housing may extend proximally, and may include a proximal connection region for connecting (and particularly, releasably connecting) to a reusable applicator handle ("reusable handle"). The connection may be a mechanical connection for coupling the treatment tip (which may be single-use or limited-use, e.g., disposable), such as a latch, snap, or the like. The treatment tip may be hollow.

The retractable treatment tip may include a retractable electrode partition that extends from within a distal end of the treatment tip housing. The retractable electrode partition may be configured to slide at least partially (or completely) into the treatment tip housing, and may extend partially out of the apparatus. In general, the retractable electrode partition may move relative to the other portions of the treatment tip, and in particular, the retractable electrode partition may move relative to the treatment tip housing and treatment electrodes (e.g., treatment needle electrodes). The treatment electrodes may be fixed relative to the treatment tip housing, or may be configured to be locked or fixed relative to the treatment tip housing in variations in which the treatment electrodes' penetration depth is fixed or adjustable, as will be described in greater detail herein. The retractable treatment tip may partially or completely enclose the treatment electrodes when the apparatus in not deployed. A distal electrically insulating cover may be present on the distal end of the retractable electrode partition. The retractable electrode partition may be configured to enclose and insulate the treatment electrodes.

All or some, e.g., the distal (e.g., subject-facing) end of the retractable electrode partition, may be electrically insulating, as mentioned. This electrically insulating distal end may be configured to be soft, and in some cases may be deformable. For example, the electrically insulating end may be a material having a durometer of 60 or less on the Shore A hardness scale (e.g., a durometer of 55 or less, a durometer of 50 or less, a durometer of 45 or less, a durometer of 40 or less, a durometer of 35 or less, or in some variations a durometer of at least or greater than about 5, 10, 15, 20, 25, 30, 35 and less than about 40, 45, 50, 55, 60, etc.). The distal electrically insulating end may also be referred to and may function as a distal contact pad for making contact between the end of the distal electrically insulating cover and the subject's tissue. As mentioned, the distal electrically insulating end is typically insulated, and may include or be entirely made of an electrically insulating material having the desired hardness, such as one or more of: silicone, santoprene, or other TPE (Thermoplastic Elastomer) materials. In some variations the distal end of the electrode partition includes an electrically insulating cover. The cover may have the softness (e.g., durometer) within the ranges described above.

The distal electrically insulating end may be connected to the distal-facing (e.g., subject tissue-facing) end of the retractable electrode partition and may therefore extend or retract with the retractable electrode partition.

The distal electrically insulating end may be of any thickness. For example, the distal electrically insulating end may be between about 0.25 mm and 5 mm, (e.g., between about 0.25 mm and 3 cm, between about 0.025 mm and 25 mm, between about 0.25 mm and 2 cm, between about 0.025 mm and 15 mm, between about 0.25 mm and 10 mm, between about 0.25 mm and 5 mm, etc.). The thickness may be uniform or non-uniform. The distal end face of the distal electrically insulating end may be flat or substantially flat. For example, the distal electrically insulating end may be shaped to include one or more protrusions (rings, or gasket-regions) around any openings for the treatment electrodes through the distal electrically insulating cover. The distal electrically insulating end may form an electrical seal against the tissue to insulate between the treatment electrodes between which energy is to be applied (e.g., a first one or more electrodes and a second one or more electrodes), and in particular between treatment electrodes of different electrical polarities. For example, in some variations treatment electrodes of different electrical polarity pass through different openings in the distal electrically insulating end (and treatment electrodes of the same electrical polarity may pass through the same openings through the distal electrically insulating end). For example, ground treatment electrodes may pass through different openings in the distal electrically insulating end than non-ground (e.g., "hot" or high/low) electrodes.

As mentioned, the treatment tip housing may include a proximal coupling region configured to couple to an applicator. The proximal coupling region of the treatment tip housing may couple the treatment tip to a hand-held applicator (a reusable treatment applicator), as mentioned. In addition, the proximal coupling region may make an electrical connection between the high-voltage, high-pulse rate generator and the electrodes in the applicator tip (e.g., the plurality of treatment needle electrodes). For example, the proximal coupling region may include a plurality of electrical connectors that are in electrical communication with the plurality of treatment electrodes.

The treatment electrodes may extend proud of the treatment tip housing (and/or proud of the electrode partition or electrode housing), in the distal direction. In some variations the treatment electrodes may extend perpendicular of the electrode partition and/or the distal electrically insulating end of the electrode partition in the deployed configuration. In some variations the treatment electrodes may extend through the distal electrically insulating end of the electrode partition. For example, the plurality of treatment electrodes may be configured to extend through an opening (or multiple openings) in the distal electrically insulating end of the electrode partition when the electrode partition is retracted. Alternatively, all or some of the treatment electrodes may be extended through the distal electrically insulating end by penetrating (e.g., making a hole, puncture, slit, etc. in) the distal electrically insulating end; these punctures, slits, or holes may reseal when the retractable electrode partition is retracted. In general, the plurality of treatment electrodes may be held within the treatment tip housing in an undeployed state when the bias holds the electrode partition distally extended from the treatment tip. Thus, the distal tips (which may be sharp, e.g., tissue-penetrating, beveled, or rounded) of the treatment electrodes may be housed entirely within the treatment tip housing and/or the electrode partition when the apparatus is not deployed, and force is not being applied to drive the retractable electrode partition proximally or at least insufficient force to overcome the threshold force for deploying).

As mentioned, in any of the apparatuses described herein, the treatment electrodes may be adjustable. For example, the distal-to-proximal length of the plurality of treatment electrodes may be adjustable. The treatment tip and/or handle to which it connects may include a control (lever, dial, button, etc.) that advances or retracts the treatment electrodes so that they may extend more or less from the retractable electrode housing or partition and/or distal electrically insulating end when the retractable electrode housing (or partition) is fully deployed. For example, the apparatus may include a screw mechanism to advance or withdraw the treatment electrodes within the tip housing and/or electrode partition.

In general, any number of treatment electrodes may be used (e.g., typically 2 or more, 3 or more electrodes, 4 or more electrodes, 5 or more electrodes, 6 or more electrodes, 7 or more electrodes, etc.). The treatment electrodes may be arranged in any configuration, including in a ring, row or two or more rows (parallel rows, crossing rows, etc.). The treatment electrodes may be any length (typically length refers to the proximal-to-distal direction), including adjustable lengths, as described above. For example, the treatment electrodes may be between about 2 mm and 10 cm long (e.g., between about 2 mm and 9 cm, between about 2 mm and 8 cm, between about 2 mm and 7 cm, between about 2 mm and 6 cm, between about 2 mm and 5 cm, between about 2 mm and 4 cm, between about 1 cm and 10 cm, between 1 cm and about 9 cm, between about 1 cm and 8 cm, between about 1 cm and 7 cm, between about 1 cm and 6 cm, etc.).

A treatment tip device for delivery of electrical therapy may include: a treatment tip housing having a proximal coupling region comprising a plurality of electrical connectors; an electrode partition extending from a distal end of the treatment tip housing, wherein the electrode partition is configured to retract proximally into the treatment tip housing; a plurality of treatment needle electrodes within the electrode partition in electrical communication with the plurality of electrical connectors; and a bias within the treatment tip housing holding and in some variations driving the electrode partition distally with a bias return force so that the plurality of treatment needs are fully enclosed within the electrode partition; a distal electrically insulating end on the distal end of the electrode partition, wherein the distal electrically insulating end comprises a soft material, further wherein the plurality of treatment needle electrodes are exposed through the distal electrically insulating end when the electrode partition is driven against a subject's tissue with a force exceeding the threshold force so that the electrode partition is driven proximally relative to the plurality of treatment needle electrodes.

Also described herein are methods of treating a subject by applying electrical energy. These methods may include using any of the devices described herein. For example, a method of applying electrical therapy to a subject may include: positioning a treatment tip against the subject's tissue so that a distal end face of an electrode partition (e.g., electrode housing) contacts the subject's tissue; driving the treatment tip distally against the subject's tissue so that an electrode partition (e.g., housing) retracts into a treatment tip housing while a plurality of treatment electrodes penetrates into the tissue distally past the distal end face of the electrode partition (e.g., housing), wherein the distal end face of the electrode partition (e.g., housing) remains against the subject's patient to prevent arcing between the plurality of treatment electrodes by electrically isolating the plurality of treatment electrodes from each other. The method may further comprise applying energy to the tissue from the plurality of treatment electrodes.

As described above, the electrode partition may be an electrode housing. In any of these methods, the distal end face of the electrode partition may comprise a soft material, e.g., a material having a durometer of 60 or less (e.g., 50 or less, 45 or less, 40 or less, etc.) on the Shore A hardness scale. The distal end face of the electrode may comprise one or more of: silicon, santoprene, or other TPE (Thermoplastic Elastomer) materials, or any other material providing a high resistance.

In any of these methods, driving the treatment tip distally may comprise driving the treatment tip with a force that is greater than a threshold force necessary to overcome a bias holding the electrode housing/partition extended from the treatment tip housing, in order to drive the electrode partition proximally relative to the plurality of treatment electrodes. In variations in which the bias provides a return force (e.g., spring), the threshold force may be referred to as a bias return force; the threshold force may be between 0.01 pounds of force and 10 pounds of force, as mentioned above.

Any of these methods may also include releasing a release lock to allow the housing/partition to be retracted proximally into the treatment tip housing.

In general, applying energy may comprise applying sub-microsecond electrical pulses. For example, applying sub-microsecond electrical pulses may comprise applying a train of electrical pulses having a pulse width of between 0.1 nanoseconds (ns) and 1000 nanoseconds (ns). In some variations, applying sub-microsecond electrical pulses comprises applying a train of nanosecond electrical pulses having peak voltages of between 10 kilovolts per centimeter (kV/cm) and 500 kV/cm. For example, applying sub-microsecond electrical pulses may comprise applying a train of sub-microsecond electrical pulses at a frequency of between 0.1 (Hz) to 10,000 Hz.

Any of the methods described herein may include coupling the treatment tip to a reusable handle by connecting at least two electrical connectors on a proximal end of the retractable treatment tip to electrical contacts on the reusable handle.

Positioning the treatment tip against the subject's tissue may comprise positioning the retractable treatment tip against the subject's skin.

The methods described herein include applying energy to treat one or more indications. Any of the methods described herein may be methods for treating (and may include one or more treatment steps for treating) one or more of: any type of cancer, whether characterized as malignant, benign, soft tissue, or solid, and cancers of all stages and grades including pre- and post-metastatic cancers (examples include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; renal cancer (e.g., renal cell carcinoma); cancer of the central nervous system; skin cancer, e.g., melanoma; lymphomas; gliomas; choriocarcinomas; head and neck cancers; osteogenic sarcomas; and blood cancer; and/or Kaposi's sarcoma); dermatological procedures (e.g., treating various dermatological conditions), such as skin cancers, aging skin, skin tumors, acne, seborrheic keratosis, keloids, molluscum contagiosum, acrocordon, psoriasis, papilloma, human papilloma virus (HPV), melanoma, melasma, sebaceous hyperplasia (SH), syringoma, congenital capillary malformation (port-wine stains), congenital nevi, melasma, actinic keratosis, dermatosis papulosa nigra, angiofibroma, cherry angioma, warts, keloids/scars, aging skin, molluscum angioma, necrobiosis lipoidica (NBL), melisma, lipoma epidermal/sebaceous cyst, basal cell carcinoma; cosmetic skin treatments, including tattoo removal, hair follicle destruction, scar/keloids reduction, fat reduction, and wrinkle reduction.

Any of the methods described herein may also or alternatively include setting a length of the plurality of treatment electrodes prior to driving the treatment tip distally against the subject's tissue.

In general, driving the treatment tip distally against the subject's tissue may include penetrating the electrically insulating cover by the plurality of treatment electrodes. Applying energy may comprise applying electrical energy without any insulating gel between the tissue and the treatment tip.

In some variations, a method of applying electrical therapy to a subject may include: positioning a retractable treatment tip against the subject's tissue, wherein the retractable treatment tip comprises an electrode partition (e.g., an electrode housing) extending from a distal end of a treatment tip housing, the electrode partition having an electrically insulting distal end, a plurality of treatment needle electrodes having distal tips that are separated by the electrode partition, further wherein the retractable treatment tip is in an un-deployed configuration in which a distal end of each of the treatment needle electrodes of the plurality of treatment needle electrodes are proximal to a distal end of the electrode partition; deploying the retractable treatment tip by moving the plurality of treatment tip electrodes and the electrode partition relative to each other so that the distal end of each of the needle electrodes of the plurality of treatment tip electrodes extend distally from the electrode partition and into the subject's tissue wherein the electrically insulating distal end is applied against the tissue to electrically isolate the plurality of treatment needle electrodes from each other; and applying energy to the tissue from the plurality of treatment needle electrodes. As mentioned above, the treatment tip apparatus may include a bias.

For example, a method of applying high-voltage nanosecond pulse electrical therapy may include: positioning a retractable treatment tip against a subject's tissue, wherein the retractable treatment tip comprises an electrode partition extending from a distal end of a treatment tip housing, the electrode partition having an electrically insulating distal end, a bias holding and in some variations driving the electrode partition distally, a plurality of treatment electrodes (e.g., treatment needle electrodes) separated by the electrode partition; pushing the retractable treatment tip against the subject's tissue with a force that is greater than the threshold force to drive the electrode partition proximally relative to the plurality of treatment electrodes while penetrating the tissue with the plurality of treatment electrodes and driving the electrically insulating distal end against the tissue to electrically isolate the plurality of treatment electrodes from each other; and applying high-voltage nanosecond electrical pulses to the tissue from the plurality of treatment electrodes.

For example, a method of applying electrical therapy to a subject may comprise: positioning a retractable treatment tip against a subject's tissue, wherein the retractable treatment tip comprises an electrode partition extending from a distal end of a treatment tip housing, the electrode partition having an electrically insulting distal end, a plurality of treatment electrodes (e.g., needle electrodes) within the electrode partition, and a bias, further wherein the retractable treatment tip is in an un-deployed configuration in which a distal tip of each of the plurality of treatment electrodes is within the electrode partition; deploying the retractable treatment tip by moving the plurality of treatment tip electrodes and electrode partition relative to each other so that the plurality of treatment tip electrodes extend distally from the electrode partition and into the subject's tissue such that the electrically insulating distal end is applied against the tissue to electrically isolate the plurality of treatment electrodes from each other; and applying energy to the tissue from the plurality of treatment electrodes.

Deploying may comprise releasing a release lock to allow the bias to drive the plurality of treatment needle electrodes distally. Alternatively or additionally, in some variations, deploying may comprise pushing the retractable treatment tip against the subject's tissue with a force that is greater than a threshold force for the bias to holding the electrode partition (e.g., electrode housing) proximally relative to the plurality of treatment electrodes.

Any of the apparatuses described herein may be used without the need for an additional insulating gel (e.g., non-conductive gel) between the subject's tissue and the apparatus, including the retractable treatment tip. For example, any of these methods may include applying energy (e.g., high-voltage nanosecond electrical pulses) without any insulating gel between the skin and the retractable treatment tip.

Any of these methods may include coupling the treatment tip (referred to herein as a "retractable treatment tip" as the electrode partition (e.g., electrode housing) region may retract away from the treatment electrodes) to a reusable handle by connecting at least two electrical connectors on a proximal end of the retractable treatment tip to electrical contacts on the reusable handle. The treatment tips described herein may be configured so that the electrical connections connect as the mechanical connection(s) are engaged. A lock or fastener may be included on either or both the treatment tip and/or reusable handle to hold the treatment tip engaged with the reusable handle. Any of these methods may include locking or removably securing the treatment tip to the handle.

As mentioned, any of the methods described herein may be methods of treating skin. For example, positioning the retractable treatment tip against the subject's tissue may include positioning the retractable treatment tip against the subject's skin. Any of these methods may comprise applying high-voltage nanosecond electrical pulses to the subject's tissue to treat one or more of: organ tissue cancer, skin cancer, cherry angioma, warts, keloids/scars, molluscum angioma, necrobiosis lipoidica (NBL), melisma, lipoma epidermal/sebaceous cyst, basal cell carcinoma, aging skin, benign tumors, and precancerous tumors. Alternatively, or additionally, these methods may be methods of any other body tissue, including non-skin tissue (respiratory tissue, lung tissue, breast tissue, liver tissue, etc.).

The length of the electrodes may be selectable. Thus, any of these methods may include selecting the length of the plurality of treatment electrodes prior to pushing the retractable tip against the subject's tissue. In some variations the length of the insulation on the electrodes may also be selectable/adjustable.

In some variations, the applicator may be pushed against the tissue with sufficient force to retract the electrode partition (e.g., electrode housing) and to drive the electrodes into the tissue. The electrodes may be driven into the tissue to a predetermined depth, which may be set by the stop (e.g., preventing the electrode partition from retracting any further, and therefore stopping the electrodes from pushing into the tissue any further. For example, pushing the retractable treatment tip against the subject's tissue with the force that is greater than the threshold force to drive the electrode partition proximally relative to the plurality of electrodes may comprise compressing a spring bias within the treatment tip housing to retract the electrode partition proximally into the treatment tip housing so that the plurality of treatment electrodes extend distally from the electrode partition. Thus, pushing the retractable treatment tip against the subject's tissue may comprise penetrating the electrically insulating end by the plurality of treatment electrodes.

The retractable treatment tip devices, particularly those having a retractable electrode partition as described herein, may reduce or eliminate arcing between the electrodes even when these electrodes are not adequately coated with a non-conductive (e.g., insulating) material, such as a non-conductive gel. Allowing the electrodes to remain retracted into the treatment tip housing (and the retractable electrode partition) when not in use or inserted into tissue may prevent arcing between the electrodes.

The apparatuses described herein may also include a soft rubber or silicone tip (e.g., an insulating cover), as described above. This insulating end may reduce arcing. For example, a soft rubber or silicone at the tip may function like a Vaseline or other non-conductive gel to reduce arcing, thereby, improving the ease of use.

Thus, also described herein are insulating covers for a electrodes (e.g., needle electrodes), the insulating cover comprising: a soft body configured to fit over the distal end of a housing for an electrode, wherein the soft body comprises an electrically insulating material having a durometer of 60 or less on the Shore A hardness scale; and a channel through the soft body configured to pass the electrode. The soft body may comprise a raised ring around the channel. The raised ring may form a gasket. The soft body may have a durometer of 45 or less. In some variations, the soft boy comprises a plurality of channels through the soft body (e.g., configured to allow passage of each of the electrodes, e.g., in the distal-to-proximal direction).

The retractable treatment tip devices may also improve the safety for the user during use or handling. With the electrodes housed within the electrode partition when not in use, accidental scratching or punctures may be avoided. The retractable treatment tip devices may also reduce the likelihood of the treatment tip getting damaged during shipping or handling.

The retractable treatment tip devices may include an adjustable electrode length, as discussed above, which may allow users to customize the depth of electrode penetration thereby customizing the depth of the lesion being treated. Alternatively or additionally, the insulation length may be adjustable by the user. Adjusting the insulation length on the electrodes may allow the user to adjust the active length, thereby customizing the depth and size of the actual treatment.

Any of the retractable treatment tip devices may also include an extrusion in the tip that helps guide the electrode straight when inserting into tissue. Longer electrode, and particularly needle electrodes, may tend to veer off course when inserting them into tissue, however, having the electrode (e.g., needle) guides may hold the electrode straighter during insertion making the treatment more consistent.

The applicator devices described herein may be used with one or more of the apparatuses (e.g., pulse generators) disclosed in any of the co-owned U.S. patent publication numbers: US 2017/0245928, US 2017/0246455, and U.S. patent application Ser. Nos. 15/444,738 and 15/347,728, all incorporated by reference herein in their entirety.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIG. 1A shows a side view. FIG. 1B is a perspective view of the distal end face, showing the electrodes exposed. FIG. 1C is a proximal end view of the apparatus of FIG. 1A. FIG. 1D shows a partially exploded view of the apparatus of FIG. 1A. FIG. 1E is an exploded view of the apparatus of FIG. 1A.

FIGS. 12C-12G illustrate an example of an expandable cam portion of a retractable treatment tip. FIG. 12C is an exploded view of the extendable cam portion of a retractable treatment tip. FIG. 12D is an assembled view of the extendable cam of FIG. 12C in a collapsed (non-expanded) configuration. FIG. 12E is an assembled view of the extendable cam of FIG. 12C in an expanded configuration. FIG. 12F shows the extendable cam in a cam housing including a sliding control for extending a retracting the cam (and therefore any electrodes coupled to the extendable cam). FIG. 12G shows the extendable cam of FIG. 12F in the cam housing in an extended configuration.

FIG. 15C also includes a guide channel region for guiding the treatment needle electrodes into the tissue.

FIGS. 16G-16L show another example of a method of using a retractable treatment tip device to treat tissue (e.g., skin tissue) in which the distal end of the retractable tip device is less soft than in FIGS. 16A-16F.

In FIG. 17A the treatment electrodes are at least partially enclosed in the insulating electrode partition that extends between a left set of electrodes and a right set of electrodes; in FIG. 17B the electrode partition is retracted, exposing the treatment electrodes and in particular, exposing the space between the left and right sets of electrodes.

In FIG. 18A, an un-deployed configuration, the treatment electrodes are separated by the insulating electrode partition that extends between a left set of electrodes and a right set of electrodes; in FIG. 18B, a deployed configuration, the electrode partition is retracted, exposing the treatment electrodes and in particular, exposing the space between the left and right sets of electrodes.

DETAILED DESCRIPTION

Figure 1A:
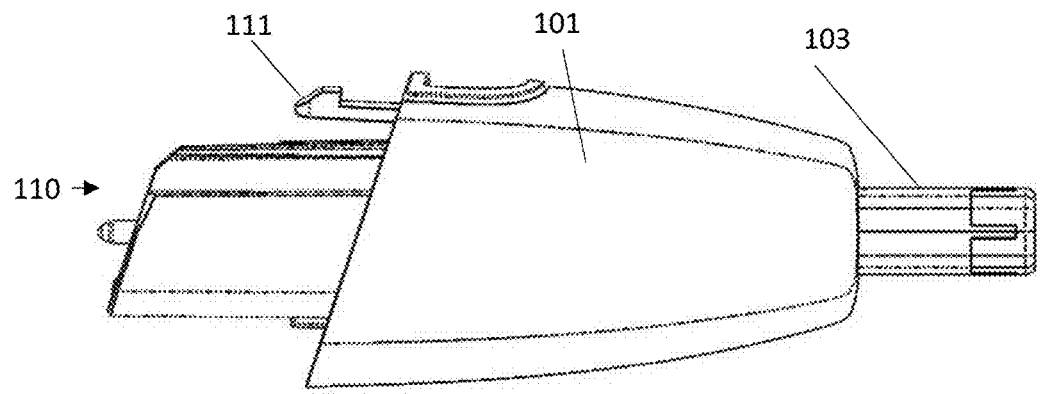
FIGS. 1A-1E illustrate a first example of a retractable treatment tip device.

The methods and apparatuses described herein generally relate to electrical treatment applications, and particularly electrode applicators having a plurality of electrodes (e.g., therapeutic electrodes, including but not limited to therapeutic needle electrodes), in which the electrodes may be electrically isolated and/or protected by an insulated electrode partition (which may be configured as a housing in some variations) in an un-deployed configuration, and may be extended into a tissue relative to the electrode partition (e.g., housing) in a deployed configuration. The electrode housing may separate and protect but does not necessary need to physically enclose the plurality of electrodes; in some variations, when the partition is configured as a housing, it may fully or partially enclose all or some of the plurality of electrodes. It should be understood that various examples referring to electrode housing are also applicable to the electrode partition and various examples referring to electrode partition are also applicable to the electrode housing, unless the context makes it clear otherwise. As will be described in greater detail, the electrode housing or electrode partition may operate as an insulating member that prevents electrical arcing between the electrodes, even without the need for additional insulating materials, such as an insulating gel, that may otherwise be required.

Some of the apparatuses as described herein include a plurality of electrodes that may be exposed by applying force to retract an electrode partition (e.g., electrode housing) relative to the electrodes (e.g., by driving the electrode housing or partition against the tissue to be treated). The electrodes may be fixed relative to a treatment tip housing, so that driving the device against the tissue drives the electrodes into the tissue and pushes the electrode housing or partition back to expose the electrodes beyond the distal end of the electrode partition (e.g., housing). Alternatively or additionally, it should be understood that the electrodes may be retractable and extendable relative to the treatment tip housing. For example, the electrodes may be coupled to a bias that can be actuated by a control on the apparatus to extend or retract the electrodes out of the treatment tip housing and/or to extend or retract the electrode housing (or partition) into the treatment tip housing. In some variations the electrode housing or electrode partition may be fixed relative to the treatment tip housing, and the electrodes may be movable. In some variations, the electrodes may be configured as part of an auto-injecting assembly in which the electrodes are biased (e.g., by a mechanical, electrical, pneumatic or other bias) against a release control (such as a button); when the release control is pressed, the electrodes may be ejected into the tissue to be treated. The electrodes may be limited by a hard stop and remain within the housing of the disposable tip.

In many of the examples provided herein the apparatus may include a bias that retains the electrode partition (e.g., electrode housing) in an un-deployed configuration with the distal face of the electrode partition, which may be soft and/or electrically insulating, extending distally beyond the distal tips of the plurality of electrodes. The bias (which may also be referred to as a retaining bias) may be overcome by applying a force greater than a threshold force. Once the applied force (e.g., by pressing the device against the tissue) is met or exceeded, the electrode partition (e.g., housing) may retract into the treatment tip housing, allowing the electrodes to extend distally beyond the distal face of the electrode partition and into the tissue. The distal face of the electrode partition (e.g., housing) may stay pressed against the tissue, helping electrically isolate the different electrodes (or sets of electrodes) in the plurality of electrodes.

In any of the apparatuses described herein, the distal-facing end of the treatment tip may be electrically insulating. Specifically, the distal (tissue-contacting) face of the electrode partition (e.g., housing) includes an electrically insulating distal end region. Furthermore, the relative movement between the plurality of electrodes and the electrode housing may allow the electrodes to be held in a protected configuration in which the distal ends of the electrodes are fully housed within the insulating electrode housing; the apparatus may then controllably convert to a deployed configuration in which the electrodes are extended out of the treatment tip housing and/or the electrode housing. In the deployed configuration, the electrodes may be fully extended to a stop position between the electrode housing and the electrodes; insulation on the distal facing end of the electrode housing may surround the electrodes, thus when pressing the apparatus into the tissue the distal facing end of the electrode housing may be pushed against the tissue when the electrodes are fully engaged with the tissue, insulating them and preventing arcing. For example, described herein are retractable treatment tip apparatuses (e.g., devices, systems, etc.) including one, or more, preferably a plurality, of electrodes that are protected by and may be enclosed inside a housing until delivery of a therapeutic treatment. These apparatuses may include a plurality of treatment needle electrodes ("needle electrodes") and be configured for the delivery of nanosecond pulsed electric fields (nsPEF, or sometimes referred to as sub-microsecond pulsed electric fields), which may include an electric field with a sub-microsecond pulse width of between 0.1 nanoseconds (ns) and 1000 nanoseconds, or shorter, for example, 1 picosecond. NsPEFs often have high peak voltages, such as 10 kilovolts per centimeter (kV/cm), 20 kV/cm, to 500 kV/cm. Treatment of biological cells with nsPEF technology often uses a multitude of periodic pulses at a frequency ranging from 0.1 per second (Hz) to 10,000 Hz. However, although the apparatuses described herein are adapted for, and particularly well suited for the delivery of therapeutic nsPEF, they may also be used as electrodes to deliver other therapeutic treatments, including treatments with continuous (non-pulsed) energy, and treatments using slower than nanosecond pulses (e.g., microsecond, millisecond, or longer duration pulses).

The apparatuses described herein may be used to deliver one or more nsPEF treatments to treat various disorders and disease, including but not limited to cancer. It has been shown that nsPEF may be used to treat cancerous tumor cells; selectively and specifically driving them to undergo apoptosis, a programmed cell death, causing tumors to shrink to nonexistence after treatment. It has also been shown that the subject's immune system may be stimulated to attack all similar tumor cells, including those of tumors that are not within the nsPEF-treated tumor. In general, a disease may include any abnormal condition in or on a subject that is associated with abnormal, uncontrolled growths of tissue, including those that are cancerous, precancerous, and benign, or other diseases as known in the art. Apoptosis of a tumor or cell includes an orderly, programmed cell death, or as otherwise known in the art.

As used herein, a "tumor" includes any neoplasm or abnormal, unwanted growth of tissue on or within a subject, or as otherwise known in the art. A tumor can include a collection of one or more cells exhibiting abnormal growth. There are many types of tumors. A malignant tumor is cancerous, a pre-malignant tumor is precancerous, and a benign tumor is noncancerous. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

In general, any of the apparatuses described herein may be connected to and used with a pulse generator. The retractable treatment tips described herein may be disposable and may be configured for a single or limited use (e.g., single use, single session use, etc.). The retractable treatment tips may be configured to connect or couple (electrically and/or mechanically) to a reusable applicator device, such as a handle connected to a control system including a pulse generator. The control system may control delivery of electrical pulses through the retractable treatment tip. These apparatuses may be particularly well adapted for delivery of high-energy (high voltage) pulse lengths, for example, of between 10 and 900 nanoseconds, including pulse lengths of between 50 and 300 nanoseconds, or about 100 nanoseconds.

For example, a nanosecond pulse generator system may include any of the retractable treatment tips described herein ("electrodes"), a user control input (e.g., footswitch) and user interface (display, monitor, speaker, etc.). The user control input and interface may be connected to the control circuitry within a housing that holds the electronic components. The retractable treatment tips may be connected to the controller and the electronic components therein through a high voltage connector. Examples of such high voltage connectors are described in the co-pending and co-owned International patent application PCT/US2017/052340, which is herein incorporated by reference in its entirety. The user may input or select treatment parameters, such as a number of pulses, amplitude, pulse duration, and frequency information, via one or more input devices, such as a numeric keypad, touch screen, mice, track pad, stylus, pen, speaker, etc.

A retractable treatment tip for high-voltage electric therapy, such as nanosecond pulse electrical therapy may include a treatment tip housing, an electrode partition, and a plurality of treatment electrodes within the electrode partition. The retractable distal tip may also comprise a distal electrically insulating cover on the distal end of the electrode partition, wherein the plurality of treatment electrodes may be exposed through the distal electrically insulating cover. In some embodiments, when the electrode partition (e.g., housing) is driven against a subject's tissue with a force exceeding a threshold force, the electrode partition may retract and the plurality of electrodes may be driven distally relative to the distal end face of the electrode partition and into the tissue. Alternatively or additionally, the electrodes may be coupled to a constrained electrode bias (e.g., needle bias) that may drive the electrodes from out of the distal end of the treatment tip housing and/or electrode partition when released from the constrained configuration. The bias constraint may be released by a button or other control (e.g., on the apparatus) activated by the user, and may drive the electrodes distally with the electrode bias force, which may penetrate the tissue if the electrode partition is pressed against the tissue.

Figure 1B:
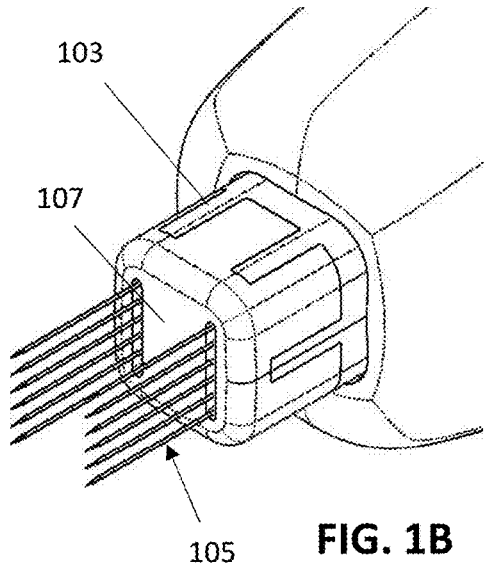
Figure 1C:
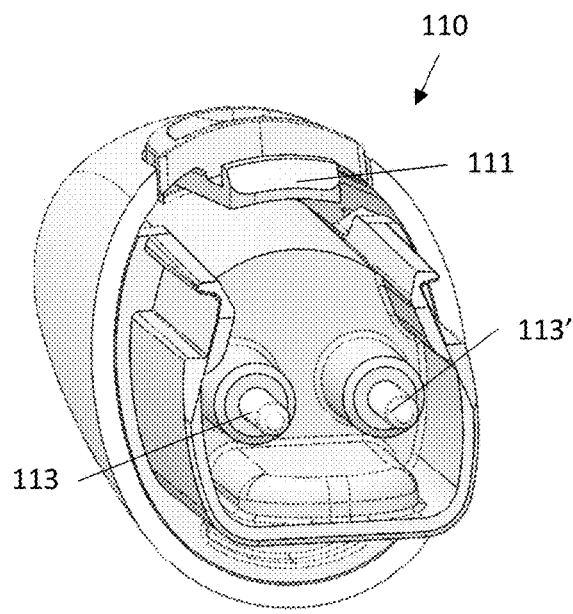
Figure 1D:
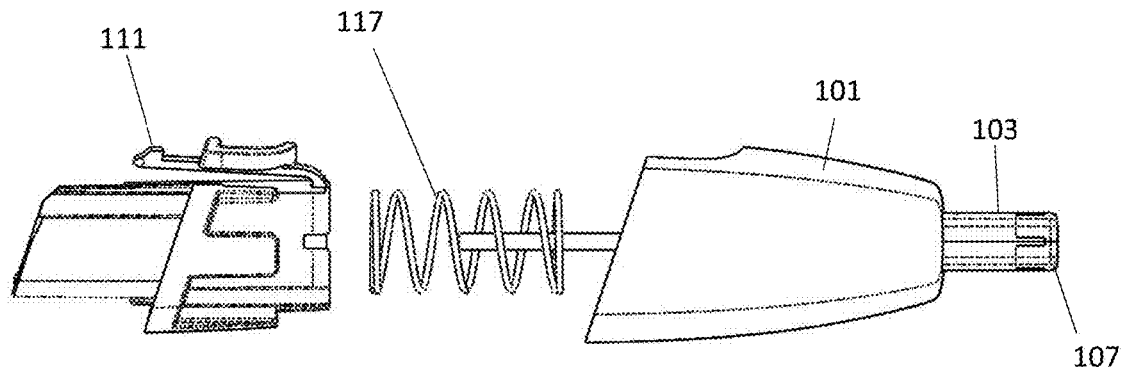

FIGS. 1A-1E illustrate one example of a retractable treatment tip. In FIG. 1A, the treatment tip is generally elongate (extending proximally to distally) and includes a treatment tip housing 101, having a slightly elongated, tapered shape. An electrode partition (configured in this example as a housing) 103 extends from the distal end of the treatment tip housing. A mechanical connector on the proximal end 110 may couple with a handle, as will be described in detail below, and may also include one or more electrical connectors for coupling with the electrodes housed within the treatment tip housing and/or electrode housing, which may extend from the treatment tip housing and/or electrode housing as shown in FIG. 1B. FIG. 1B shows a close-up of the electrode housing 103, which is shown having a rectangular cross-section (any shape cross-section may be used). The distal-facing (e.g., tissue facing) end of the electrode housing may be covered by an insulating cover 107. A plurality of treatment needle electrodes 105 are shown projecting from the at least partially retracted electrode housing. In FIG. 1B, the electrodes are needle electrodes that may have a sharp and beveled distal end but are cylindrical needles. However, the needle electrodes are shown by example only and any type and shape of electrode may be used. The electrodes may be insulated or un-insulated; in some variations the treatment electrodes are insulated along a portion of their length, but the distal end (e.g., the distal 0.5 mm, 1 mm, 1.2 mm, 1.5 mm, 1.7 mm, 2 mm, etc.) are un-insulated. FIG. 1C shows the proximal end 110 of the retractable treatment tip. In this example, the retractable treatment tip includes a mechanical connector 111 (shown by example as a snap or latch) that couples the retractable treatment tip to a handle. The retractable treatment tip also includes two electrical connectors 113, 113'. This proximal end of the retractable treatment tip may couple with the handle to make both mechanical and electrical connection.

Within the retractable treatment tip housing 101, in some embodiments the plurality of electrodes may form part of an electrode assembly that is coupled to the treatment tip housing so that the electrodes are locked in position relative to the treatment tip housing, but not the electrode housing 103. In this example, a bias 117 (shown in the partially exploded view of FIG. 1D by example as a spring) may be used to apply a bias return force against the electrode housing, to push the electrode housing distally. The electrode housing 103 may engage with the treatment tip housing 101 so that it can otherwise slide proximally and distally. For example, the electrode housing and treatment tip housing may slide relative to each other via a channel formed in the treatment tip housing in which a projecting region in the electrode housing slides. Alternatively or additionally, the channel may be in the electrode housing and the projection may extend from the treatment tip housing. In general, the bias may hold the electrode housing distally extended until it reaches a stop position; in some variations a mechanical stop may be included to prevent further distal advancement. The electrode housing may be driven proximally by applying force (typically normal to the distal-facing end of the electrode housing) to the electrode housing. For example, by pushing the distal facing end of the electrode housing against the tissue when holding the treatment tip housing (e.g., coupled to a handle).

Figure 1E:
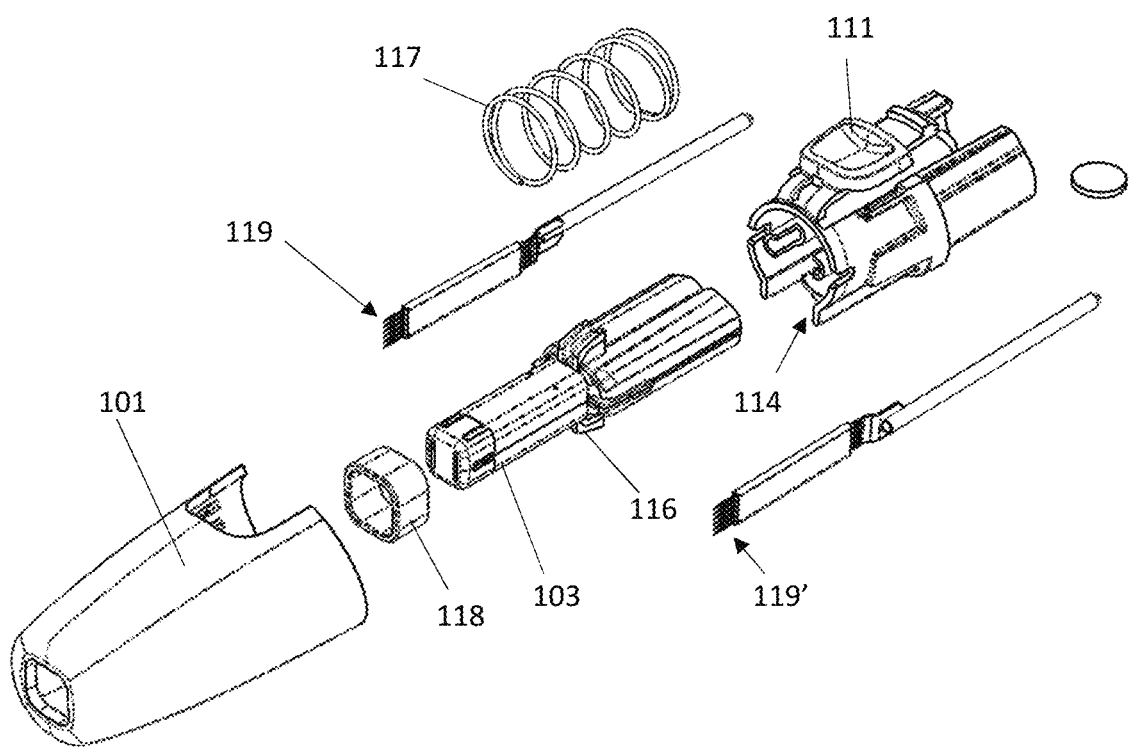

FIG. 1E is an exploded view of the retractable treatment tip example shown in FIGS. 1A-1D. The distal portion of the treatment tip housing 101 connects with a proximal portion 114 of the treatment tip housing to enclose the bias 117 and at least a portion of the electrode housing, as well as the plurality of electrodes (e.g., a first set of one or more electrically connected needle electrodes 119, and a second set of one or more electrically connected needle electrodes 119') and electrical connectors (not shown). In this example, the mechanical connector 111 may be used to couple the retractable treatment tip to a handle (e.g., a reusable handle). In the example of FIG. 1E, the electrode housing includes projections 116 that slide within the outer treatment tip housing 101, e.g., in channels within the treatment tip housing. A spacer 118 may be used to limit the relative movement between the treatment tip housing and the electrode housing. The two halves of the outer treatment tip housing may be connected permanently or removably.

The retractable treatment tips described herein may come in a variety of different sizes and configurations that may be used in multiple indications. For example, the size (e.g., diameter) of the treatment area on the distal face of the apparatus may be varied (e.g., between about 1 mm to 20 mm), and may be any appropriate shape (e.g., rectangular, rounded, triangular, oval, etc.). The treatment electrodes (e.g., needle electrodes) may be any appropriate length, and may be a fixed length or the length may be adjustable. For example, the length may be between about 0.2 mm and 60 mm. The diameter of the electrodes may be any appropriate diameter, e.g., a maximum cross-sectional diameter of between about 0.02 and 1 mm. The treatment electrodes may be insulated. The distal-facing (e.g., flat or beveled) face is typically not insulated, but in some variations a distal-facing length of the treatment needle electrodes extending from the distal end of the treatment needle proximally may be uninsulated as well. For example, the distal end of the electrode may be uninsulated to leave an exposed length of between about 0 mm and 20 mm. The length of the insulation may be variable and/or adjustable. For example, the length of the insulation of the electrodes may be controllably adjusted to between about 0 mm and about 20 mm.

Figure 2A:
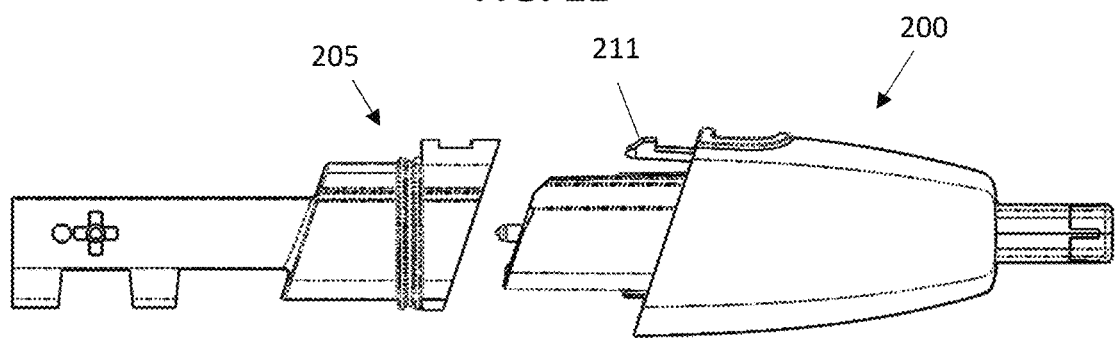
FIG. 2A is a view of the retractable treatment tip device (similar to the one shown in FIG. 1A) before coupling with a portion of a handle including a mechanical and/or electrical connection.
Figure 2B:
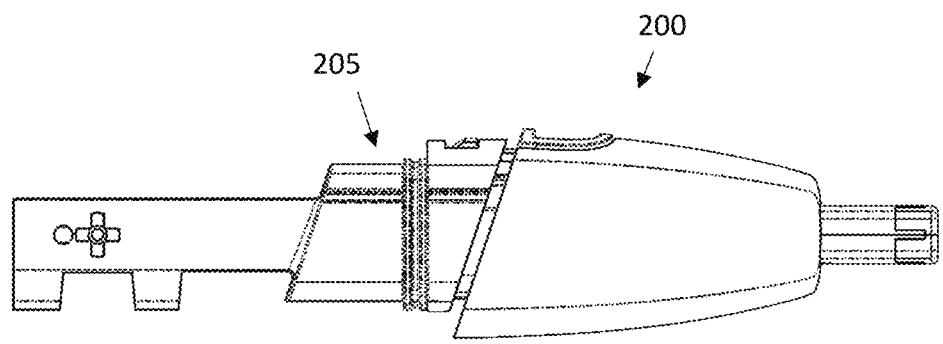
FIG. 2B shows the retractable treatment tip device engaged with the portion of the handle.

As mentioned, the retractable treatment tip (e.g., a disposable treatment tip) is generally configured to couple with a reusable handle. FIGS. 2A-2B illustrate mechanical and electrical coupling between a retractable treatment tip 200 and a portion of a reusable handle 205. A connector 211 (shown by example as a clip in FIGS. 2A-2B) may mechanically and releasably secure the retractable treatment tip and the handle together.

The retractable treatment tips may be configured to attach to any appropriate handle, as will be shown in greater detail in FIGS. 8A-8B and 9, below.

Figure 3A:
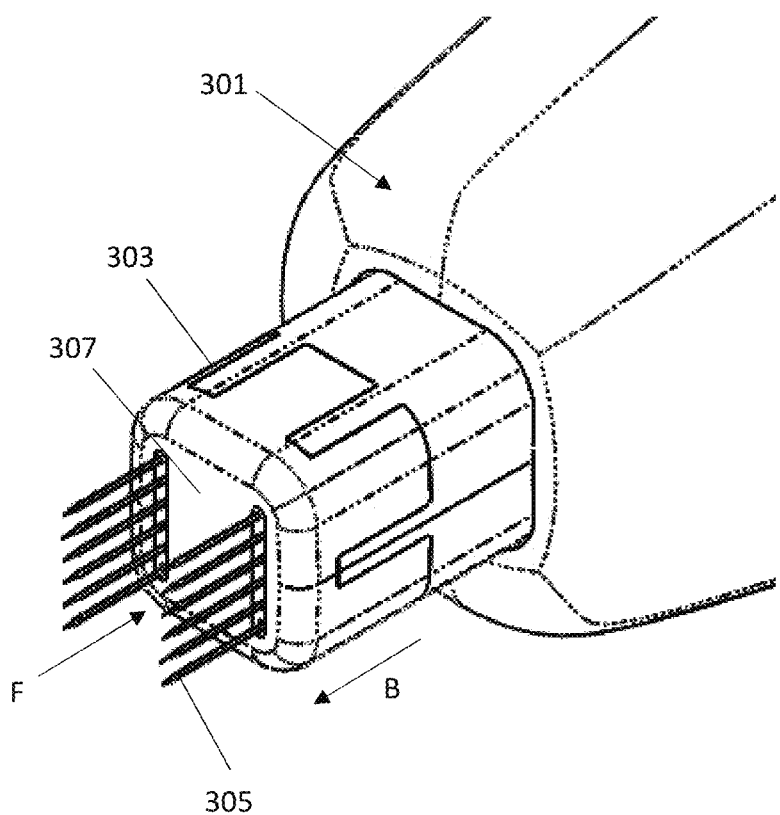
FIG. 3A is an enlarged perspective view of an example of a distal end of a retractable treatment tip device, showing the plurality of exposed needle electrodes.
Figure 3B:
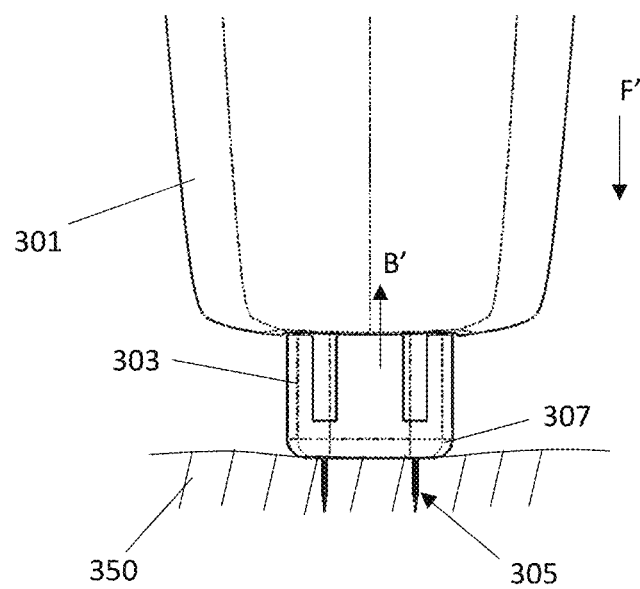
FIG. 3B shows an example of a side view of a retractable treatment tip device applied to tissue with a force against the tissue sufficient to cause the electrode housing (or electrode partition) to retract as the treatment needle electrodes are driven into the tissue.

FIG. 3A shows another view of an example of the distal end of a retractable treatment tip, including an insulating cover 307 that covers the distal-facing end of the electrode housing 303 with a layer of soft, insulating material. The electrode housing 303 may be held distally out of the treatment tip housing 301 by a bias (e.g., a spring in this example) that is capable of applying a biasing return force B (shown in FIG. 3A), but pushing against the biasing return force (e.g., by driving the retractable treatment tip against the tissue to be treated while holding the handle to which the retractable treatment tip is coupled) may push the electrode housing proximally allowing the treatment electrodes to be driven distally into the tissue. In FIG. 3A, the needle electrodes 305 are shown deployed out of the electrode housing, presumably because a force greater than the threshold force to overcome the bias (e.g., "F" in FIG. 3A) is applied against the distal face of the electrode housing 307. In practice, this may be achieved by pushing against a tissue. This is illustrated in FIG. 3B. In this example, the threshold force is equivalent to the biasing return force, B'. The apparatus shown in FIGS. 3A-3B is held proximally by a handle or by the treatment tip housing portion and force, F, is applied to drive the electrode housing 303 against the tissue 350 by pushing the device into the tissue. This allows the electrodes 305 to be driven into the tissue 350 while pushing the soft insulating cover 307 portion of the apparatus against the tissue between the electrodes, insulating them relative to each other. As the electrode housing is retracted into the treatment tip housing 301, the electrodes extend into the tissue. The bias return force B' (arrow in FIG. 3B) opposing the applied force F', and sine the applied force is greater than the threshold force (in this case B'), the electrode housing is retracted while the needle electrodes are extended into the tissue. In this example, the electrode housing distal face is driven against the skin with the bias return force B'.

Figure 4A:
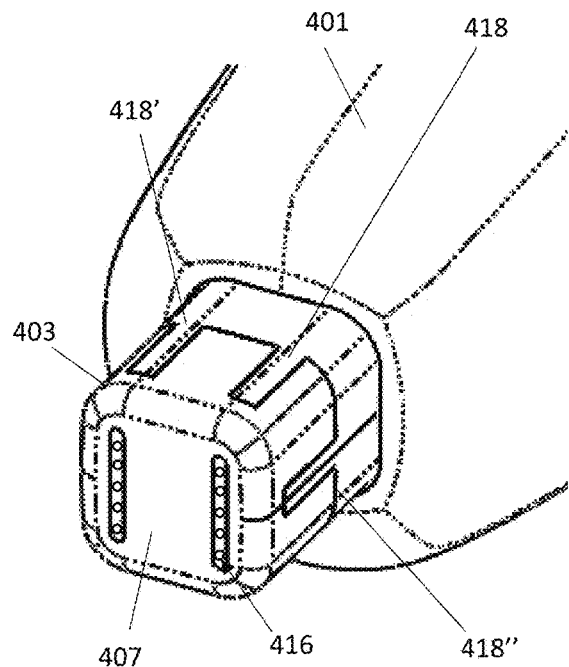
FIG. 4A shows an example of an enlarged perspective view of a distal end face of a retractable treatment tip device in which the treatment needle electrodes are fully enclosed in the electrode housing.
Figure 4B:
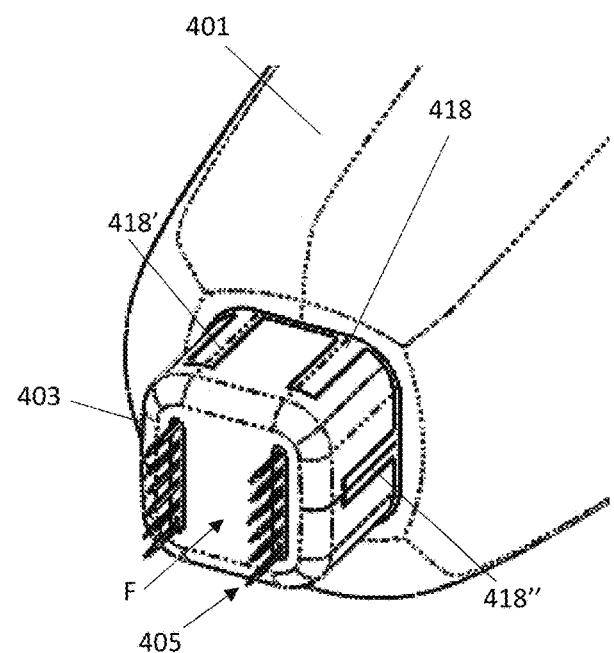
FIG. 4B shows the retractable treatment tip device of FIG. 4A with a force sufficient to overcome the bias holding the electrode housing portion of the retractable treatment tip device distally, exposing the treatment needle electrodes.

FIGS. 4A and 4B illustrate another example of a retractable treatment tip. In FIG. 4A the distal end of the apparatus is shown with the electrode housing 403 fully extended distally. An internal spring (not shown) may bias the electrode housing distally, holding it in the un-deployed configuration and providing a bias return force to restore the un-deployed configuration. The electrode housing may include a distal insulating cover 407 that, in this example, has a plurality of openings or holes 416 through which treatment electrodes 405 may extend when the housing is pushed (by a force greater than the threshold force, in this example equivalent to the biasing force) into the distal end of the treatment tip housing 401. In this example the side of the electrode housing may include one or more fiducial markers 418 that mark the relative position of the electrode housing relative to the treatment tip housing 401 and/or the relative position and orientation of the treatment electrodes on the tip. For example, in FIGS. 4A and 4B, the two fiducial lines 418, 418' on the tops of the electrode housing 403 are aligned with the rows of needle electrodes once they exit the electrode housing. In this way, the user may know where the rows of needle electrodes are. The fiducial line 418" on the adjacent side is in the middle of the two rows of needles. The top of these lines may indicate the fully retracted position of the electrode housing and/or the fully extended position of the needle electrodes when deployed. Some or all of these fiducial markers (e.g., lines) on the electrode housing, or other markers on the electrode housing, may show how far the electrode housing is retracted, and/or how far the electrodes have been inserted into the tissue. For example, lines transverse to the elongate length (e.g., of fiducial lines 418, 418', 418") may include indicators for the electrode depth. The fiducial markers described in reference to FIGS. 4A and 4B may be used in any of the examples, embodiments and implementations described herein.

Figure 5A:
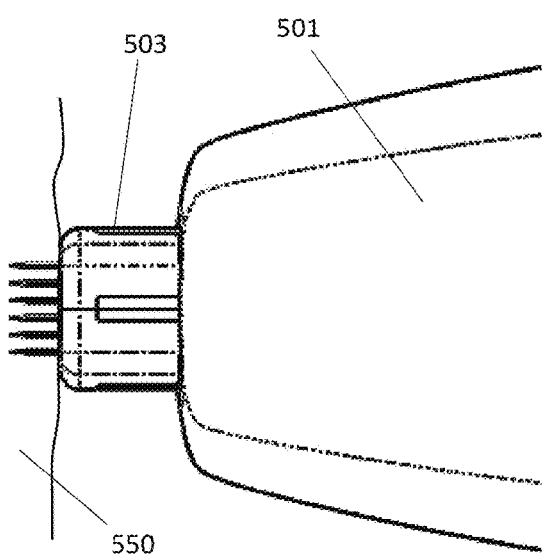
FIG. 5A shows a side view of an example of a retractable treatment tip device driven against the tissue so that the sharp treatment needle electrodes are inserted into the tissue while the electrode housing is biased against the tissue (e.g., skin).
Figure 5B:
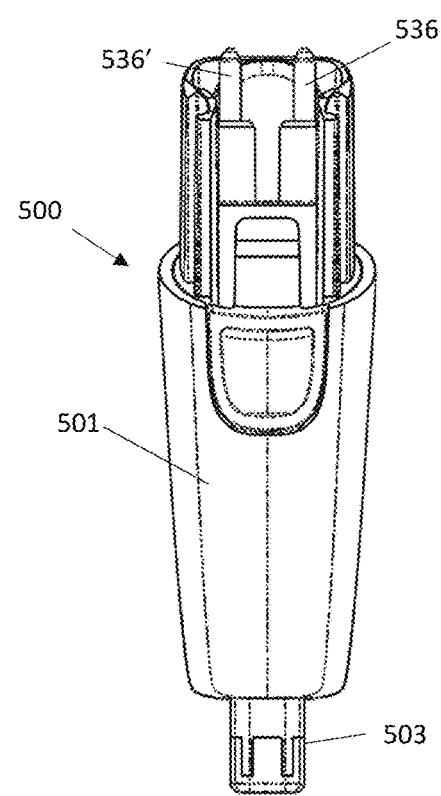
FIG. 5B is a side view of an example of a retractable treatment tip device in an un-deployed configuration.

FIGS. 5A-5B illustrate another example in which the treatment tip is pushed against a tissue 550 with sufficient force to drive the treatment electrodes into the tissue as the electrode housing 503 is pushed proximally and the soft, insulating distal face of the electrode housing is driven against the face of the tissue being treated so that it retracts into the treatment tip housing 501, as shown. In FIG. 5B, the apparatus 500 is shown in the un-deployed configuration. Two electrical connectors 536, 536' are also shown on the proximal end of the apparatus, shown in this example as male connectors that connect to the treatment electrodes.

Figure 6A:
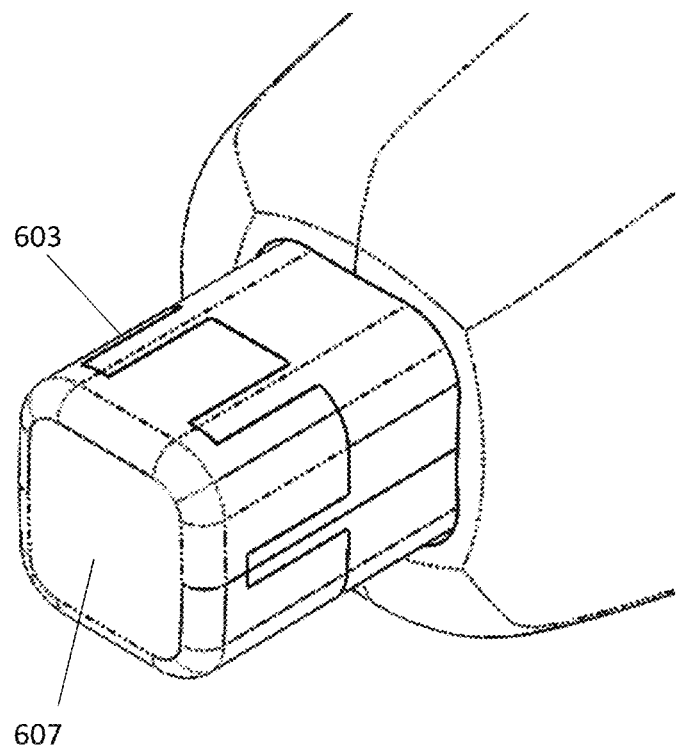
FIG. 6A illustrates an example of a distal end of a retractable treatment tip device including an insulating cover through which electrodes (e.g., needle electrodes) may be driven, as shown in FIG. 6B.
Figure 6B:
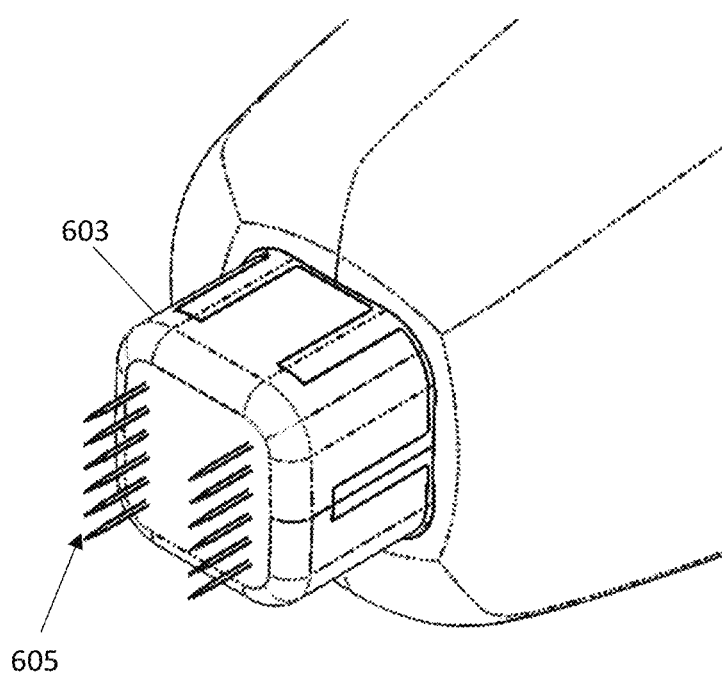

In the example shown in FIGS. 4A and 4B, above, the distal end of the electrode partition is covered by an insulating cover that includes holes or opening through which the electrodes may extend when the electrode housing is pushed proximally. In some variations the insulating cover does not include holes or openings and instead the treatment electrodes penetrate into and through the soft insulating cover itself. For example, the soft insulting cover may be silicone, santoprene, or other TPE (Thermoplastic Elastomer) materials. This is illustrated in FIGS. 6A-6B. In FIG. 6A the soft insulating cover 607 is smooth, and does not yet have any openings through it. Retracting the electrode housing 603 by pushing against it with sufficient force to overcome any bias from, e.g., a spring within the housing, as well as the force required to penetrate the thickness of the insulating cover allows the treatment electrodes 605 to extend out of the insulating cover, as shown in FIG. 6B.

Figures 7A, 7B:
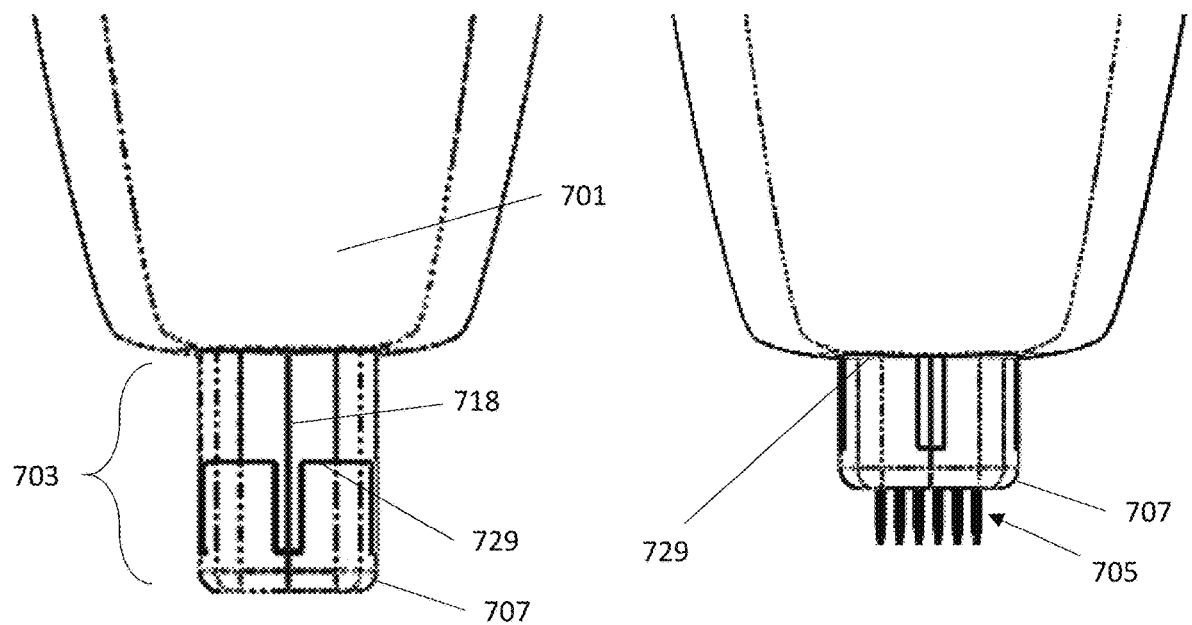
FIG. 7A is an example of a distal end of a retractable treatment tip device in an un-deployed configuration.
FIG. 7B shows the distal end of the device in a deployed configuration, in which the electrode housing/partition and insulating cover are retracted to expose the needle electrodes.

FIGS. 7A and 7B illustrate another example of a distal end of a retractable treatment tip device in which the apparatus includes a plurality of treatment needle electrodes 705 extending through a thickness of soft insulting cover 707 forming the distal end of the electrode housing 703 that extends distally from the distal end of the treatment tip housing 701. In FIG. 7A, the border 729 of the insulating cover 707 which may extend partially up the lateral side of one or more of the sides of the electrode housing may be used to confirm deployment (e.g., retraction of the electrode housing and insertion of the needle electrodes into the tissue). As shown in FIG. 7B, when applied against the tissue (not shown), the border 729 may align with the distal end of the treatment tip housing 701 when the needles 705 are fully deployed. Alternatively or additionally, when the two parts of insulating cover 707 that wrap around the fiducial line 718 can be longer and when those two wrap-around features are in-line with the treatment tip housing 701, the needles are fully deployed. Thus, in any of the variations described herein, a fiducial marking (e.g., line) may indicate that the electrodes are fully deployed. This may be particularly beneficial, as the electrodes may be fully deployed into the tissue and not visible to the user. A visual indicator that the electrodes are fully deployed may be used to determine when treatment should be triggered.

Figure 8A:
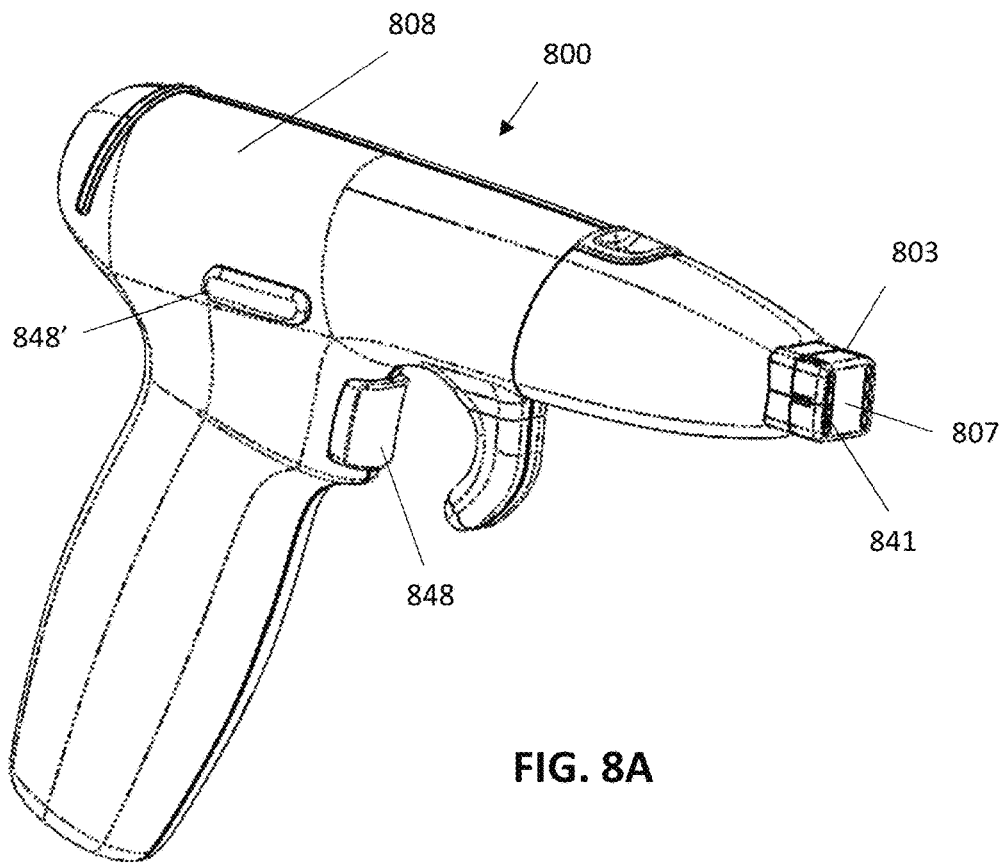
FIGS. 8A and 8B illustrate examples of retractable treatment tip devices, configured as disposable tips, coupled to a reusable handle applicator portion configured as a gun.
Figure 8B:
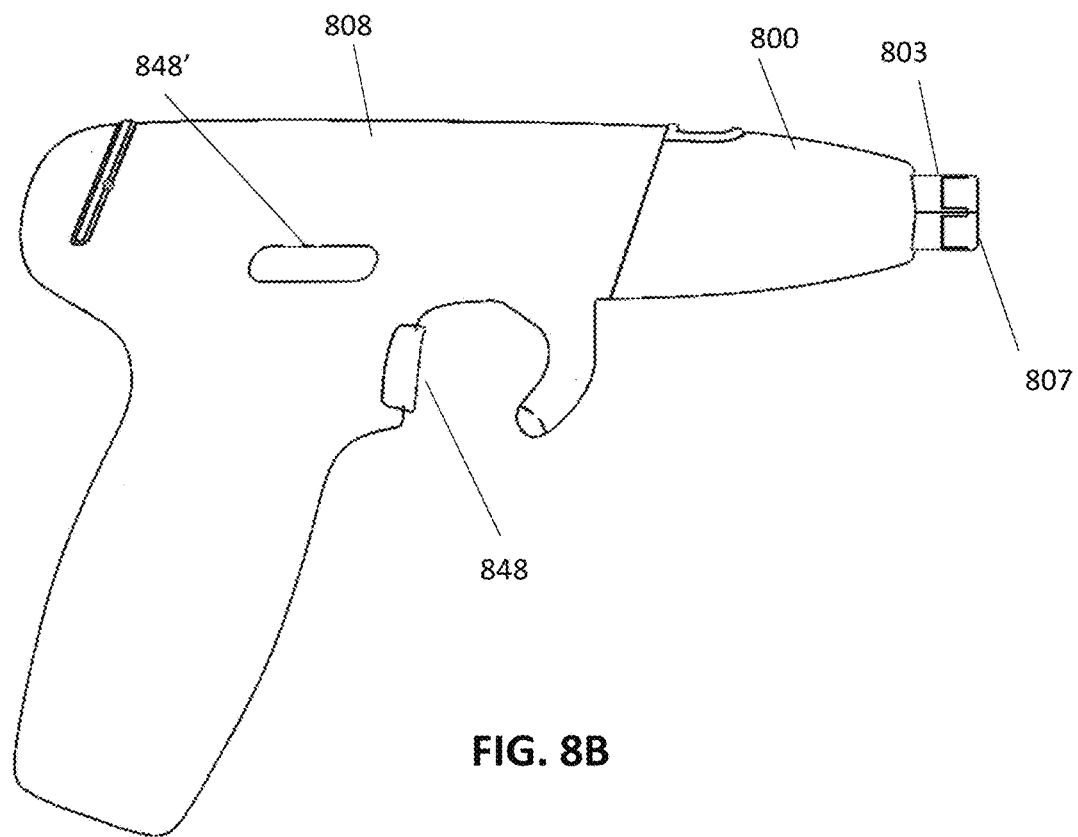

FIGS. 8A-8B illustrate a first example of a reusable handle for an nsPEF applicator system. In FIGS. 8A and 8B, the handle 808 is configured as a gun-shaped body that couples to a treatment tip 800, as shown. The treatment tip includes an electrode partition 803 (including an insulating, distal-facing portion 807 that may be soft and/or compliant). The electrode partition includes openings 841 through which the treatment electrodes may extend. The reusable handle may include one or more controls 848, 848' that may be used to control the delivery of electrical energy through the electrodes. In some variations the apparatus may be configured to prevent or limit the application of energy through the treatment electrodes until and/or unless the electrode partition is retracted (or retracted past a particular depth) or the electrodes are extended (or at least partially extended). The applicator handle shown in FIGS. 8A-8B may be connected (e.g., via a cable or cables, not shown) to a pulse generator and/or controller.

Figure 9:
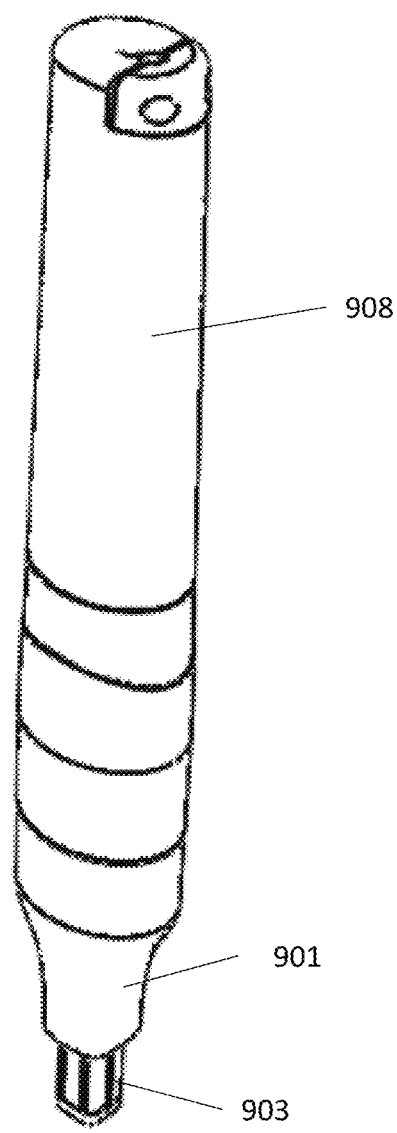
FIG. 9 is another example of a retractable treatment tip device coupled to a reusable handle applicator configured as a pen.

FIG. 9 illustrates another embodiment of a reusable applicator handle 908, for example, for an nsPEF that couples (mechanically and/or electrically) to a treatment tip 901 having a retractable electrode partition 903, which may be similar to any of those electrode housings discussed above or similar to a partition 1803 shown in FIG. 18 below. In this example, the applicator handle may be a pen or a cylinder-shaped body. One or more controls (not shown) for controlling the depth of penetration of the treatment electrodes, e.g., a dial, lever, slider, etc. that moves the stop for the treatment housing and/or the relative position of the electrodes within the treatment tip housing.

Figure 10:
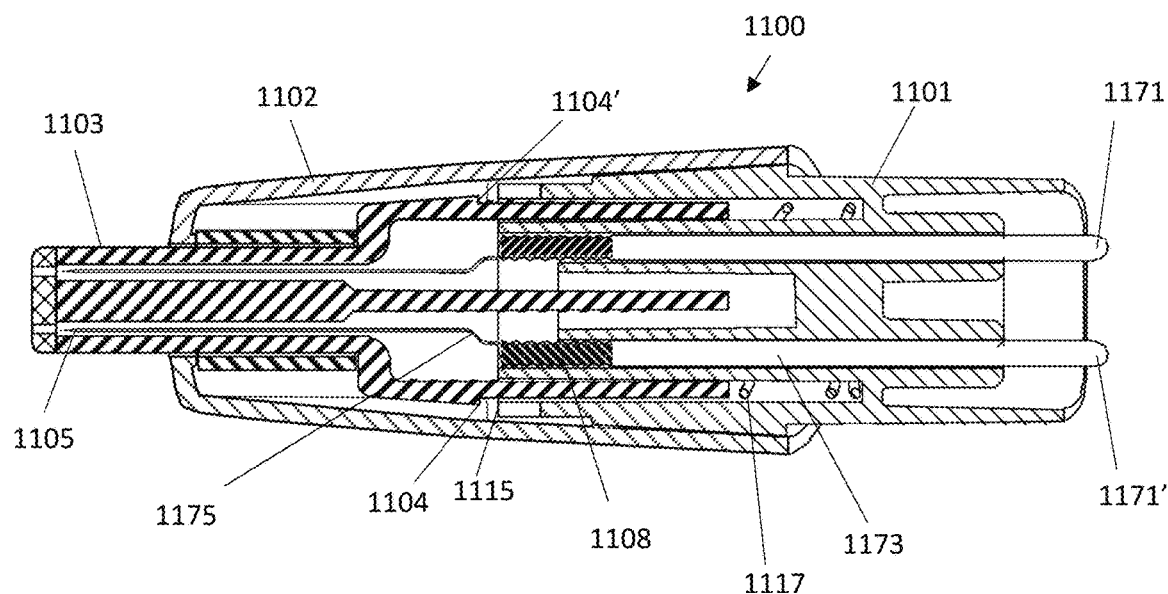
FIGS. 10 and 11 show sectional views through one example of a retractable treatment tip device in an un-deployed (FIG. 10) and a deployed (FIG. 11) configuration.
Figure 11:
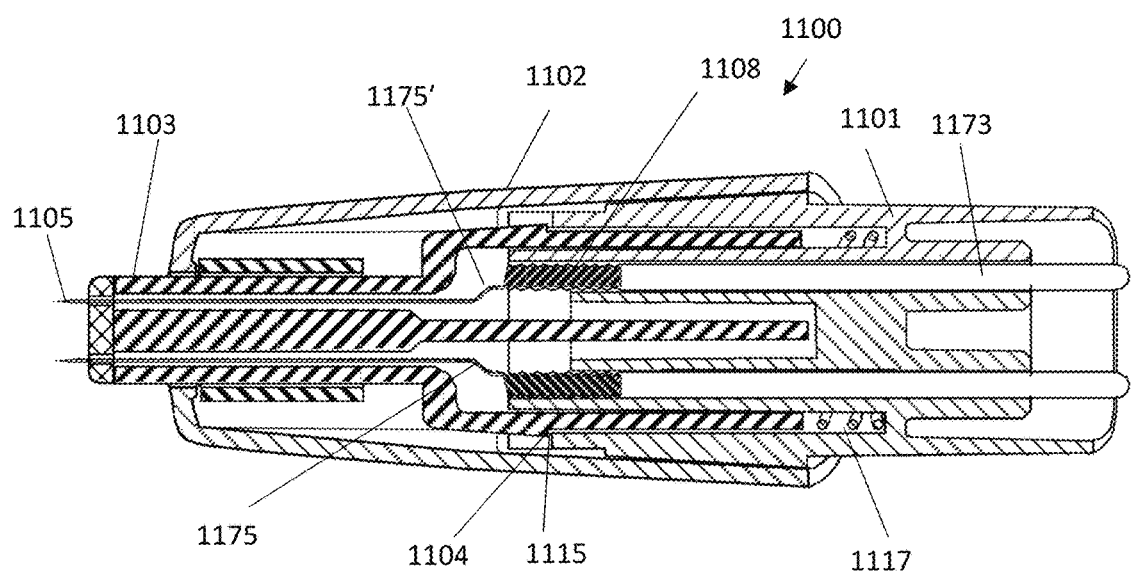

The treatment tip may include a plurality of electrical connectors that each connect one or more treatment electrodes to the pulse generator through the reusable handle. For example, FIGS. 10 and 11 illustrate treatment tips 1100, shown in cross-sectional views, that include a pair of electrical connectors 1171, 1171' that are wired 1173 (e.g., vie wire, post or other electrical connector) to connect to the treatment electrodes 1105, as shown in FIG. 11. In the sectional view shown, the bias 1117 is connected between the treatment tip housing 1102, 1101 (formed from two connected portions) and the retractable electrode partition 1103 (configured as a housing in this example). The bias in this example is a spring. The treatment tip housing may include an internal stop 1115 for limiting the proximal movement of the electrode partition, as shown in FIG. 11B, in which the electrode housing is fully retracted when a force that is greater than the threshold force driving the electrode partition distally is applied. The stop 115 engages a lip, rim or edge 1104 on the housing. The treatment needle electrodes (electrodes) may form an electrode assembly 1175, 1175' that in some embodiments may be coupled 1108 to the treatment tip housing so that it does not move relative to the treatment tip housing as the treatment tip is driven distally with sufficient force to retract the electrode partition. In the retracted state, the electrode array (e.g., needle electrode array) sits at the distal end of the tip, recessed inside the soft, elastomeric tip in some variations (e.g., the insulating distal end region). The proximal end of the needle array shown in FIGS. 10 and 11 includes electrical connectors configured as male pin terminals that may connect to the handle. The apparatus may include a spacer (not shown) that may limit the fully extended position of the electrode partition within the treatment tip housing in the un-deployed configuration.

Figure 12A:
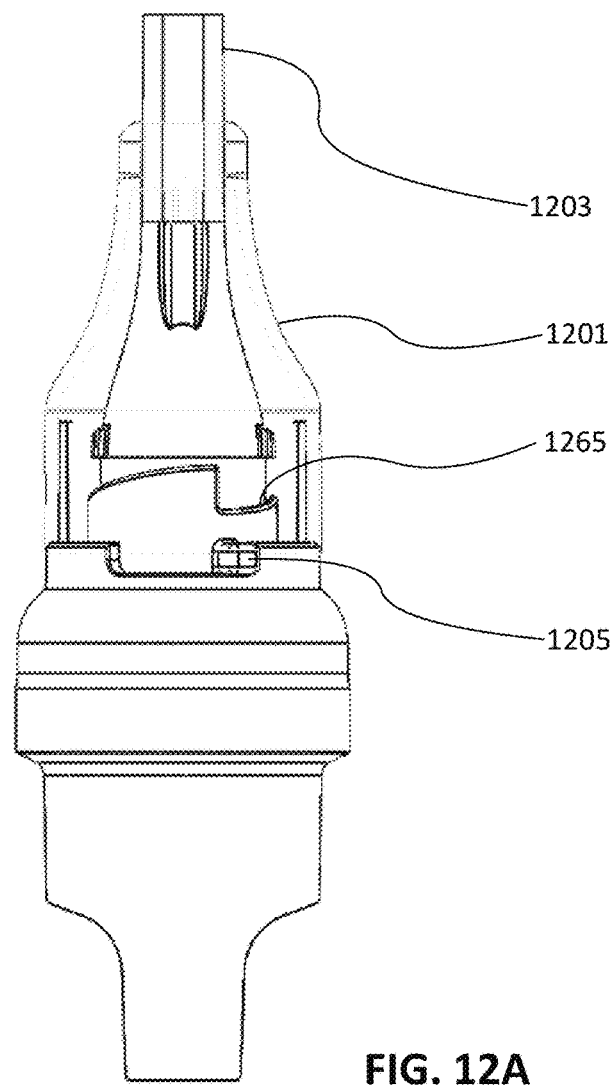
FIG. 12A is a schematic example of a retractable treatment tip device having an adjustable needle length.

As discussed above, in any of the treatment tips described herein, the penetration depth of the treatment electrodes may be adjustable. For example, the length of the treatment tip electrodes that extends from the electrode partition when the retractable electrode partition is fully retracted may be adjustable. FIG. 12A illustrates one example of a treatment tip including an adjustable electrode length. In FIG. 12A, a control (dial 1205) on the treatment tip allows it to be adjusted by rotating a ramp or surface 1265 within the treatment tip. Either or both the electrode assembly position may be adjusted, e.g., adjusting the relative positions of the treatment electrodes within the treatment tip housing 1201, or the position of the stop for the proximal retraction of the electrode partition 1203 into the treatment tip housing 1201 may be adjusted. For example, by rotating a dial (such as dial 1205 in FIG. 12A), the stop location may adjust proximally/distally and may change the total electrode deployment length. In any of the variations shown herein, the length of the insulation on all or some of the treatment electrodes may be adjusted by a control (e.g., dial, slider, knob, etc.) on the treatment tip.

Figure 12B:
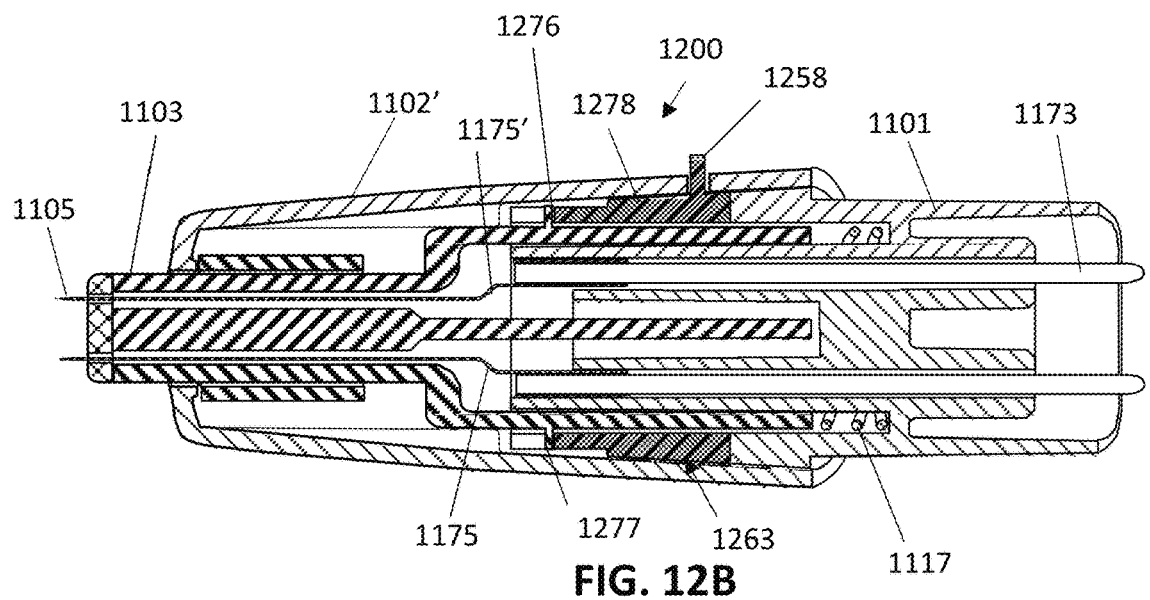
FIG. 12B is a sectional view through a retractable treatment tip device similar to that shown in FIG. 12A, having an adjustable needle length.

FIG. 12B shows a cross sectional view of another example of a treatment tip 1200 having adjustable length electrodes, similar to that shown in FIG. 12A. In FIG. 12B the device includes many of the same elements as in FIG. 11 (e.g., electrodes 1105, electrode housing 1103, treatment tip housing 1102', 1101, electrode assembly 1175, 1175', electrical connectors 1173, and bias 1117). However, in FIG. 12B, the device may also include an expandable cam portion including a cylindrical cam assembly 1263 with one or more ramps and a control tab lever 1258 shown in cross section. The cylindrical cam follower 1278 portion of the cylindrical cam assembly 1263 may be positioned between a modified proximal housing 1102' and the electrode housing 1103, and may include one or more controls (e.g., control tab/lever 1258) extending through a slot 1212 (see FIG. 12F-12G, not visible in FIG. 12B), in the distal housing portion. FIGS. 12C-12G show an example of a cylindrical cam assembly 1263 that may be used for extending or retracting the electrodes. The cylindrical cam assembly 1263 may be similar to that shown in FIG. 12B. An electrode assembly may include one or more guide/stop tabs 1276, 1277 (seen in FIG. 12B) that when retracted may ride on top of (come in contact with) the surface of the cylindrical cam follower 1278, such that the retraction stop dimension may be set by the position of the cylindrical cam rotational position as controlled by control tab (lever) 1258.

For example, in FIG. 12C a schematic perspective view of one example of a cylindrical cam assembly 1263 includes an outer cylindrical cam 1255 having two ramps 1256, 1257 on its distal circumference. A control tab (lever) 1258 may be integral with the cylindrical portion of the of the cylindrical cam element. The electrodes (electrode assembly) may be in contact with either the top or bottom of the cylindrical cam assembly (e.g., the cam follower 1278 or the outer cylindrical cam 1255), while the other one of the top or bottom of the cylindrical cam assembly 1263 may be connected to the tip housing or other reference surface. For example, the cylindrical cam follower 1278 portion of the cam assembly 1263 may include two guide/stop tabs 1270, 1271 on opposing sides of the electrode partition. The guide/stop tabs 1270, 1271, may move within axial guide slots (cam surfaces) in an inner wall of a distal housing (not shown in FIG. 12C-12D, but see FIGS. 12F-12G), and may not rotate. The guide/stop tabs 1270, 1271 may ride on the top of the respective complimentary cam ramps 1256, 1257 causing the electrode assembly and/or the electrode housing to extend and retract or move in a distal or a proximal direction relative to the treatment tip housing as the control 1258 is moved.

FIG. 12D is a schematic perspective view of the extendable cam assembly 1263 shown in FIG. 12C. In FIG. 12D, the inner cam follower 1278 is engaged with the outer cylindrical cam 1255 having its control (e.g., knob or lever) 1258 rotated to a position where the guide/stop tabs 1270, 1271 ride on the top of the respective complimentary cam ramps 1256, 1257 to their lowest (most proximal position). In FIG. 12E, when the control (e.g., lever) 1258 is rotated (as shown by the arrow from right to left in FIG. 12G) to a most extended control position, the guide/stop tabs 1270, 1271 ride on the top of the respective complimentary cam ramps 1256, 1257 to a highest (most distal) location, extending the extendable cam.

FIGS. 12F and 12G include an outer housing 1211 outside of the inner 1278 and outer 1255 cylindrical cam elements. The outer housing may be part of or connected to the treatment tip housing. In FIG. 12F, a slot 1212 in the outer housing 1211 is visible, through which a control 1258 can extend.

Figure 13A:
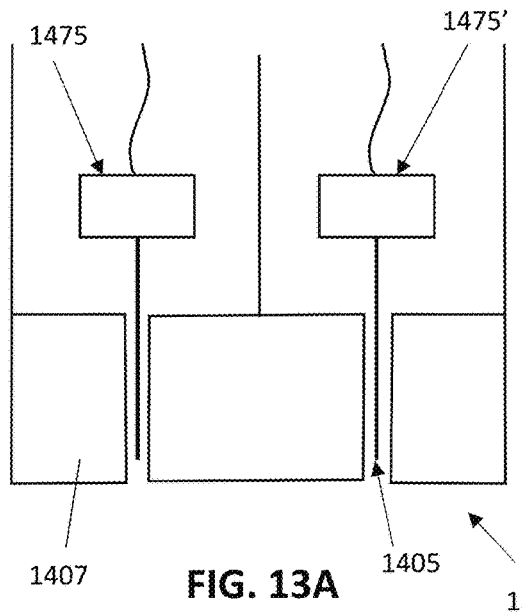
FIGS. 13A-13B schematically illustrate variations of the distal ends of retractable treatment tip devices including different insulating cover regions.

In use, the distal end of the soft distal end of the electrode partition may be configured as an insulator. This insulator may be an insulator cover, as described above, or it may be the material from which the entire electrode housing or electrode partition, or at least a distal end portion of the electrode housing or electrode partition, is formed. FIGS. 13A-13B and 14A-14B illustrate alternative variations of electrode insulators, including distal insulators and covers. In FIG. 13A the distal end face of the electrode partition 1309 is an insulator 1407 that is formed of a soft material that can be driven against the tissue. The insulator may include openings for one or more of the treatment electrodes 1405, shown connected to an electrode assembly 1475, 1475'. The soft insulator 1407 may be pushed against the tissue and may conform to the tissue surface, even if the tissue surface is slightly irregular.

Figure 13B:
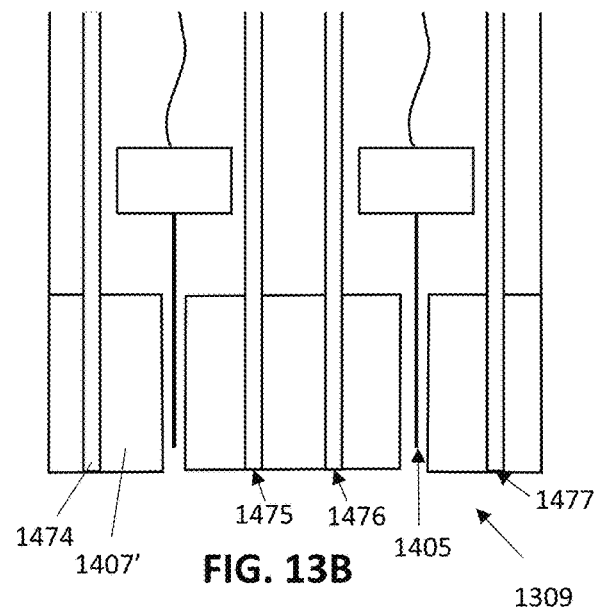

In some variations the distal end face of the electrode partition may include one or more vacuum ports through which suction may be drawn to help secure the electrode partition against the tissue to prevent shorting (arcing) between the treatment electrodes. In FIG. 13B, the insulator 1407' includes passages forming the suction ports 1474, 1475 1476, 1477. The ports may extend via tubing (e.g., flexible tubing) up to a suction source in the handle or controller. In other embodiments, the suction ports that help to secure the electrode partition against the tissue to prevent arcing may be used on their own without the insulator. In those embodiments, the suction ports may be formed through the electrode partition to the distal end of the electrode partition.

Figure 14A:
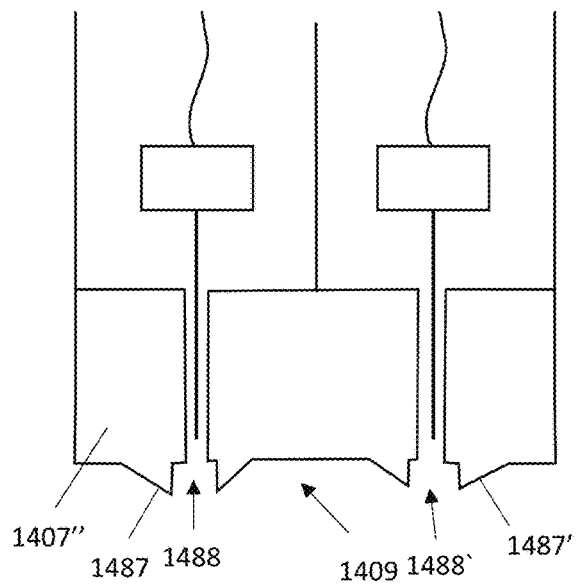
FIGS. 14A-14B schematically illustrate further examples of variations of the distal ends of retractable treatment tip devices including different insulating cover regions.

In FIG. 14A, the retractable electrode partition 1409 includes a soft, insulating distal face (shown as a cover 1407") that includes a sealing region 1487, 1487' around the distal-facing treatment electrode openings 1488, 1488'. In some variations these sealing regions are projections and may be ring-shaped or continuous around the openings to permit them to seal and electrically insulate the treatment electrodes.

Figure 14B:
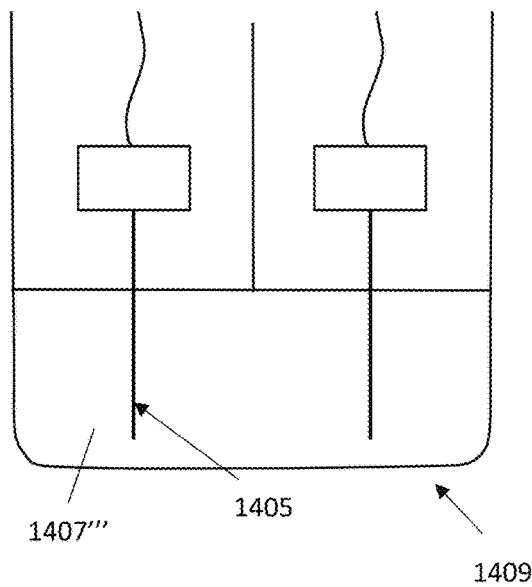

As discussed above in reference to FIGS. 6A-6B, in some variations the insulating cover may not include defined openings, but may be configured to be penetrated by the treatment electrodes when the electrode housing/partition is retracted or the electrodes are extended. Another example of this configuration is shown in FIG. 14B, showing an insulating cover 1407''' that is solid, but may be formed of a material that can be penetrated by the treatment electrodes 1405.

Figure 15A:
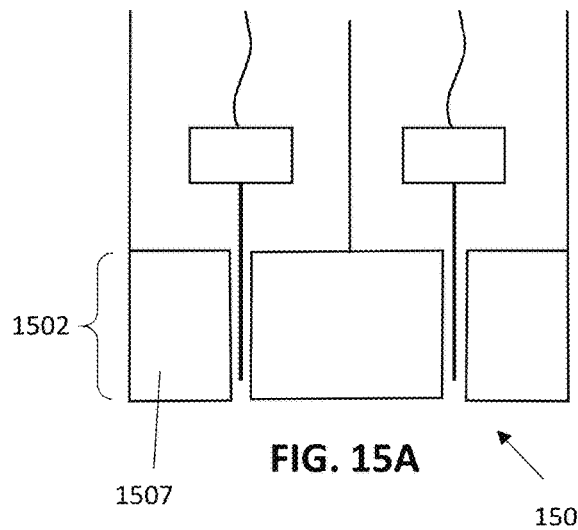
FIGS. 15A-15C schematically illustrate variations of the distal ends of retractable treatment tip devices including different thicknesses of soft insulating cover regions.
Figure 15B:
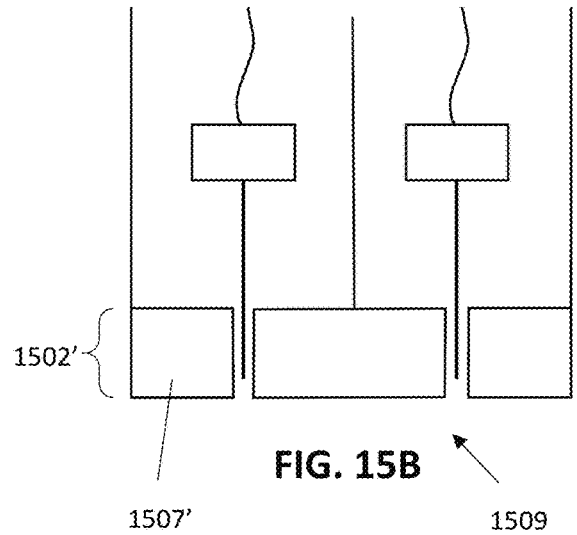
Figure 15C:
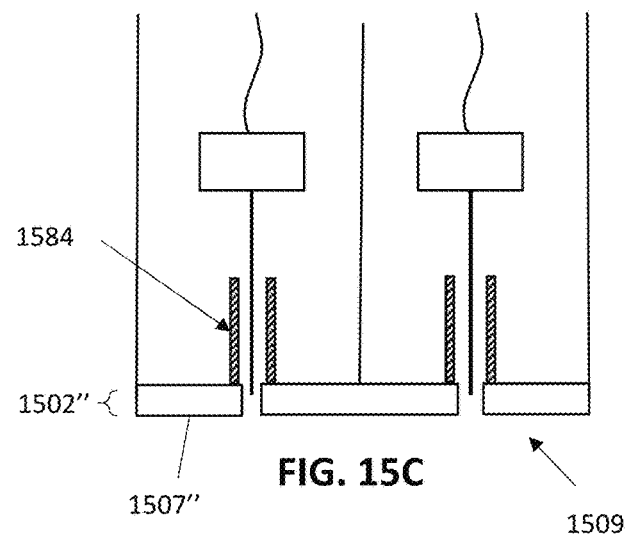

In general, the insulator (e.g., insulating cover or insulating distal end) of the retractable electrode partition may be any appropriate thickness. In some variations, particularly those in which the insulating distal end/cover are relatively thin, a guide (e.g., electrode guide, needle electrode guide, etc.) may be included to guide the electrodes as they extend through and out of the treatment tip housing and/or electrode partition, preventing bending. For example, FIGS. 15A-15C illustrate retractable electrode partitions 1509 having soft, insulating covers of varying thicknesses 1502, 1502', 1502". The variation of the insulating cover 1507 shown in FIG. 15A is similar to that shown in FIG. 13A. For comparison, FIG. 15B shows an example of an apparatus having a slightly thinner 1502' soft, insulating cover 1507'. Finally, in FIG. 15C, the soft insulating cover 1507" is thinner 1502" than that shown in FIG. 15B. In FIG. 15C the electrode partition also includes an electrode guide 1584 (or a plurality of electrode guides). The electrode guides may be proximal to the soft, insulating cover, and may be made of a more rigid material. In variations in which a separate insulating cover is used at the distal face of the electrode partition, the insulating cover may be any appropriate thickness. For example, the insulating cover may have a thickness (in the distal-facing direction) of between about 0.25 mm and 5 mm.

In use, any of the apparatuses shown herein may be configured to apply energy (e.g., nsPEF) to a tissue. For example, any of these apparatuses may be used to treat a tissue such as skin, liver, lung, breast, etc., or treat a disorder or disease such as cancer. For example, any of these apparatuses may be configured to apply energy to treat a disease, for example, a disease related to dermatology and/or oncology, such as skin cancer, cherry angioma, warts, keloids/scars, aging skin, molluscum angioma, necrobiosis lipoidica (NBL), melisma, lipoma epidermal/sebaceous cyst, basal cell carcinoma.

Figure 16A:
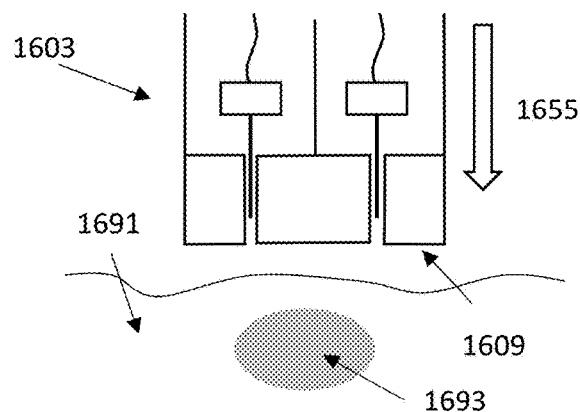
FIGS. 16A-16F illustrate an example of a method of using a retractable treatment tip device to treat tissue (e.g., skin tissue).
Figure 16B:
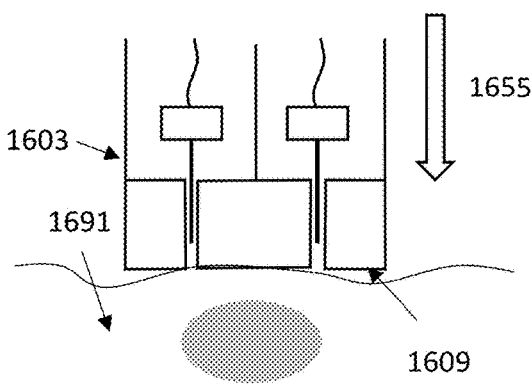
Figure 16C:
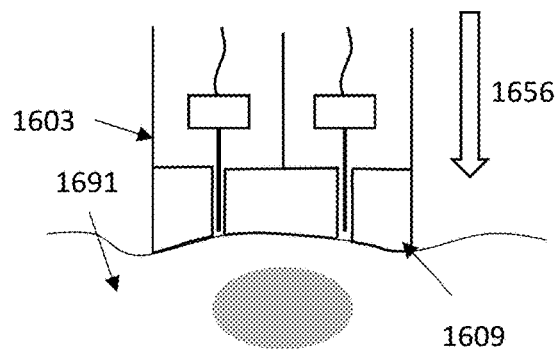
Figure 16D:
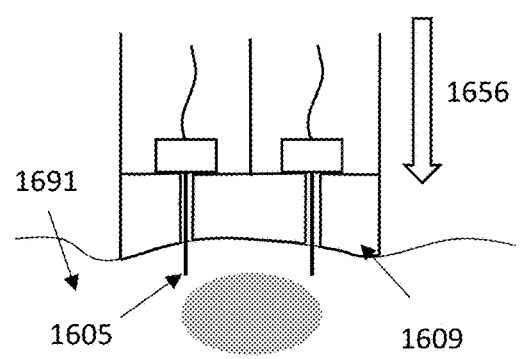
Figure 16E:
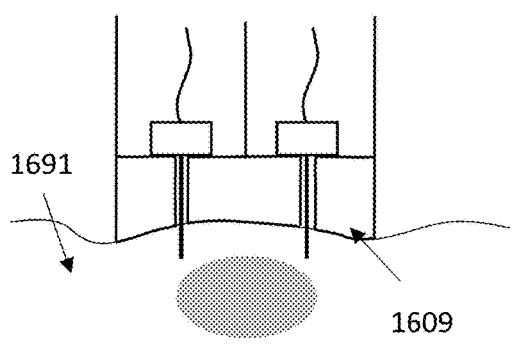
Figure 16F:
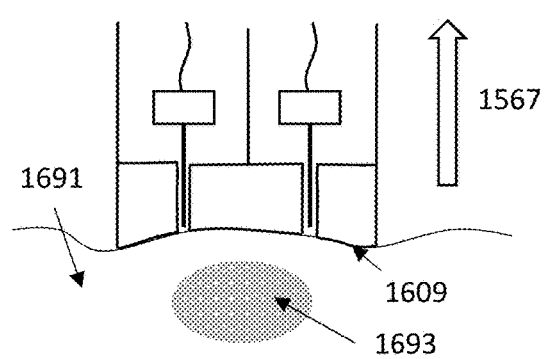

The use of an applicator tip having a retractable electrode housing or electrode partition as described herein may be particularly beneficial. For example, the apparatus may be configured to conform to an irregularly-shaped or textured surface while preventing arcing, which may otherwise be dangerous and painful to the subject. For example, FIGS. 16A-16F illustrate the use of a retractable (biased) electrode partition extending from the distal end of the apparatus. In FIG. 16A, the distal end of the applicator tip 1603 is brought in proximity to the tissue 1691, in which a target region 1693 to be treated is present. Thus, the entire applicator tip may be driven with force 1655 against the tissue, as shown in FIGS. 16B-16C, first to contact the tissue, then to continue to apply force 1656, which may allow the soft (e.g., semi-compliant) distal-facing insulator of the applicator tip 1603 to conform to the surface of the tissue 1691 to be treated. Distally-directed force 1656 may be applied, as shown in FIG. 16D, to drive the electrodes 1605 into the tissue while pushing and retracting the electrode partition proximally, allowing the electrodes to penetrate the tissue and the insulator to insulate between them. Once the electrodes have been positioned (in this example in FIG. 16E to a maximum depth allowed by the retracted electrode partition), power, including in particular nsPEF therapy, may be applied. Thereafter, the applicator tip may be withdrawn, as shown in FIG. 16F by arrow 1657; any therapeutic effect on the treatment site 1693 may result either immediately or within a reasonably short time period.

In FIGS. 16A-16F, the distal-facing, soft insulating end (e.g., cover) on the electrode partition 1609 is sufficiently soft that it deforms to fit the tissue, as shown in FIGS. 16B-16C. For example, the durometer of the soft, insulating cover may be less than about 60 or less on the Shore A hardness scale (e.g., about 55 or less, about 50 or less, about 45 or less, about 40 or less, etc.). Alternatively, in some variations the hardness of the insulating cover may be greater than the hardness of the tissue, so that the tissue may deform (or both the tissue and the soft insulating cover may deform). FIGS. 16G-16L illustrate an example in which the tissue and the soft insulating cover both deform. In FIG. 16G, the distal end of the applicator tip 1603' is brought in proximity to the tissue 1691', in which a target region 1693 to be treated is present. Thus, the entire applicator tip may be driven with force 1655 against the tissue, as shown in FIGS. 16H-16I, first to contact the tissue, then to continue to apply force 1656, so that the distal-facing insulator of the applicator tip 1603 pushes against the surface of the tissue to be treated; in this example, the tissue deforms slightly to match the applicator. The distal-facing insulating end of the electrode partition may not be soft (e.g., semi-compliant) or it may be compliant. Thus, the electrode partitions described herein may include a soft distal cover or may just be an insulating material (that is not compliant). Distally-directed force 1656, as shown in FIG. 16J, drives the electrodes 1605 into the tissue while pushing and retracting the electrode partition proximally, allowing the electrodes to penetrate the tissue and the insulator to press against the tissue and insulate between the electrodes. Once the electrodes have been positioned (in this example in FIG. 16K to a maximum depth allowed, for example, by the retracted electrode partition), as shown in FIG. 16K, power, including in particular nsPEF therapy, may be applied. Thereafter, the applicator tip may be withdrawn, as shown in FIG. 16L by arrow 1657; any therapeutic effect on the treatment site 1693 may result either immediately or within a reasonably short time period.

Figure 17A:
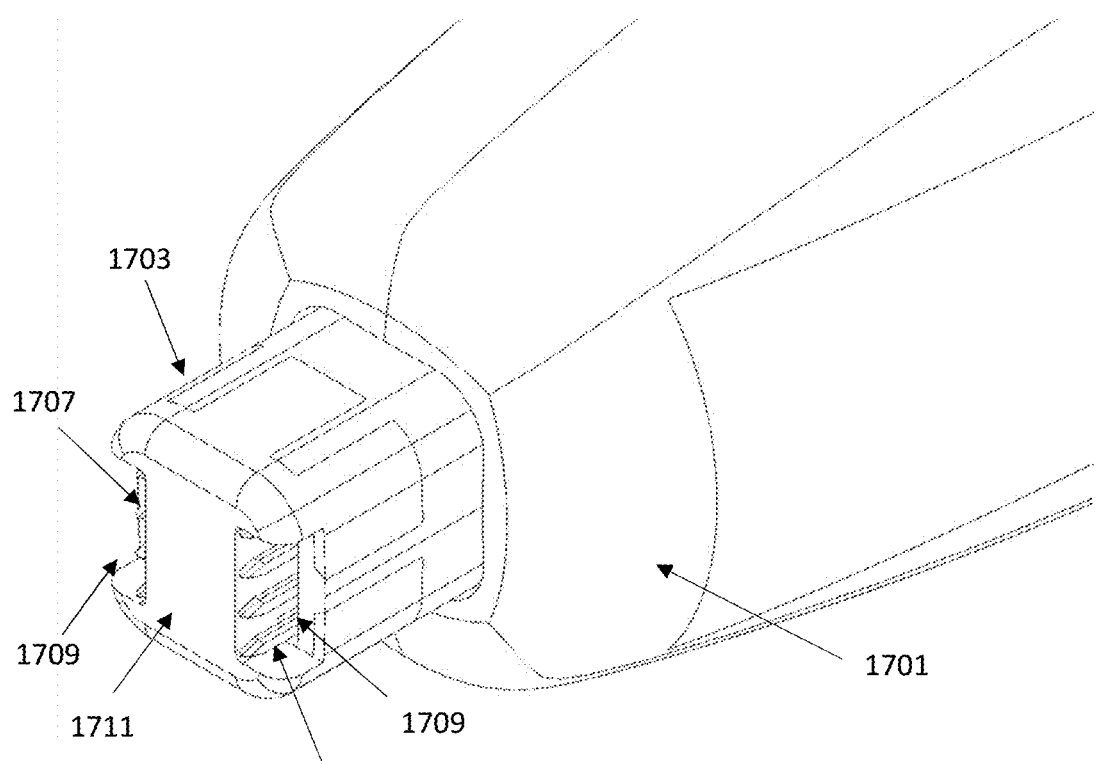
FIGS. 17A and 17B show a perspective view of one variation of a distal end face of a retractable treatment tip device.
Figure 17B:
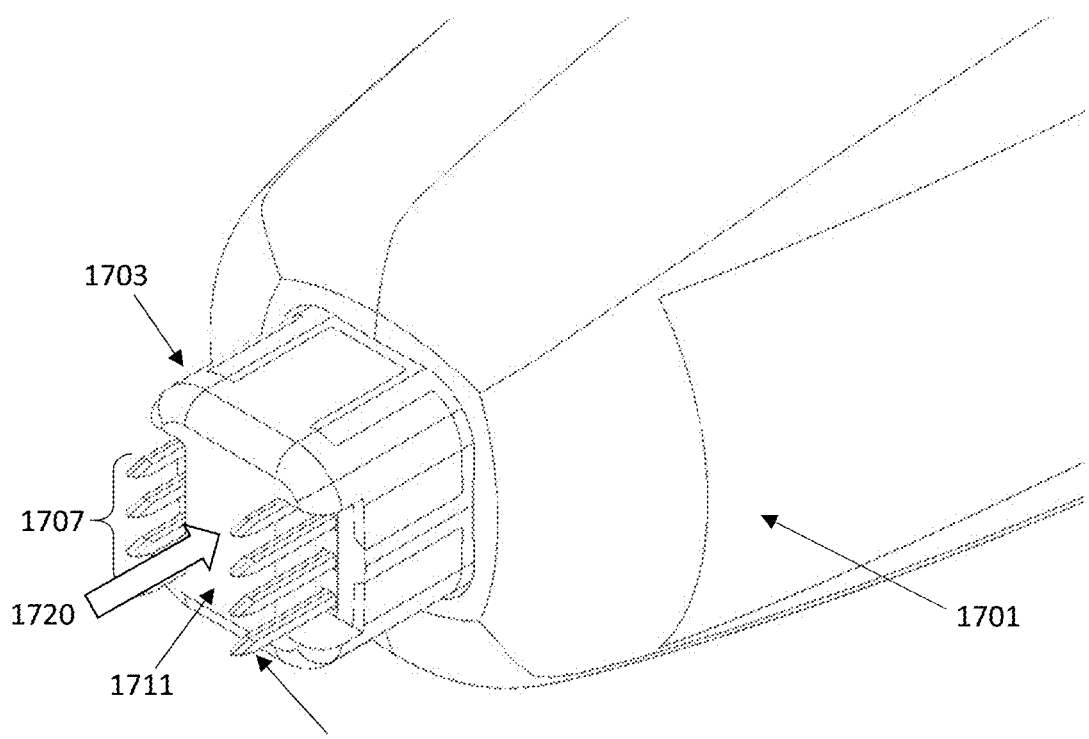

FIGS. 17A-17D illustrate another example of a treatment tip device for delivery of electrical therapy. The device includes a treatment tip housing 1701 and an electrode partition 1703 that extends from a distal end of the treatment tip housing. The electrode partition 1703 includes one or more lateral cut-outs or window openings 1709. The lateral sides of a first set of electrodes 1705 and a second set of electrodes 1707 are visible through these lateral cut-outs or window openings in an un-deployed or pre-treatment configuration. Thus, the device includes a plurality of treatment electrodes; in this example, the treatment electrodes are needle electrodes. The treatment electrodes may include a first one or more treatment electrodes (e.g., four are shown on the left in FIG. 17A), and a second one or more treatment electrodes (e.g., four are shown on the right in FIG. 17A) separated from the first one or more treatment electrodes by the electrode partition. The electrode partition in this example is similar to the electrode housing of FIGS. 3A, 4A-B. The electrode partition may be formed of an insulating material (entirely or at least at the distal end of the partition. In particular, the region between and/or adjacent to the treatment electrodes may be formed of an electrically insulating material. The distal end face 1711 of the electrode partition 1703 may be relatively soft (e.g., may have a durometer of 60 or less on the Shore A hardness scale). In FIG. 17A, the cut-outs or window openings(s) 1709 on the lateral sides of the electrode partition extend to the distal end face 1711. In some variations the window openings may not extend all the way to the distal end face, for example, such that the tips of the electrodes are not visible in the window openings in the un-deployed configuration but may be beneath a cover as described above. In FIG. 17A the lateral window openings extend only partially along the sides of the electrode partition; in some variation the lateral window openings may extend more or less along the sides of the electrode partition. In some variations the lateral side is open (e.g., the cut-out or window opening extends down the entire side of the electrode partition, as shown in FIGS. 18A-18B). In FIGS. 17A and 17B, by example, the two lateral cut-outs show the distal end regions of the first one or more electrodes 1705 and the second one or more electrodes 1707. In some variations a smaller cut-out(s) allowing visualization of subsets (or individual) electrodes may be included; in some variations each electrode may be visible through a lateral window.

In FIG. 17A, the device is shown with the electrode partition in an un-deployed configuration in which the distal ends of the first one or more treatment electrodes are separated from the distal ends of the second one or more treatment electrodes by the electrode partition. FIG. 17B shows the device in a deployed configuration in which the plurality of treatment electrodes 1705, 1707 extend distally beyond the electrode partition (e.g., distally beyond the distal end face 1711 of the electrode partition). As described above, the electrode partition and treatment electrodes may be configured to move relative to each other to convert between the un-deployed and the deployed configurations. In FIGS. 17A and 17B the electrode partition retracts at least partially (e.g., about 40%) into the treatment tip housing. As described above, a bias within the treatment tip housing may exert a force (e.g., a bias return force) to oppose conversion from the un-deployed to the deployed configuration or from the deployed to un-deployed configuration; in this example, a force (arrow 1720) may drive the electrode partition 1703 into the treatment tip housing 1701 when the force is greater than the threshold force.

Figure 17C:
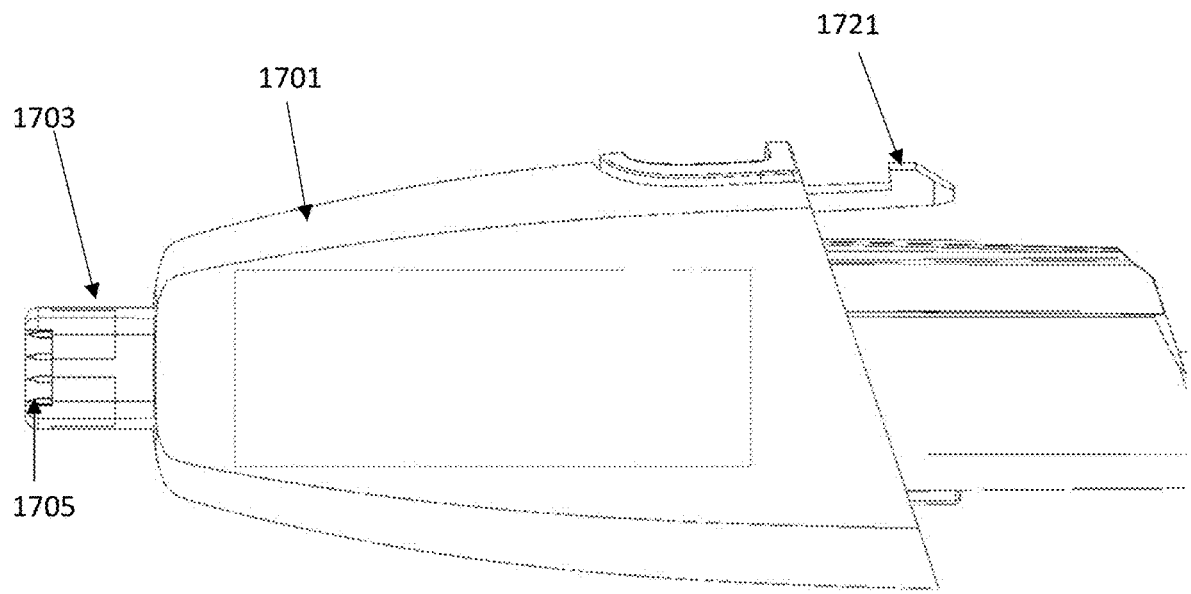
FIGS. 17C and 17D show side views of a variation of the retractable tip apparatus of FIGS. 17A and 17B.
Figure 17D:
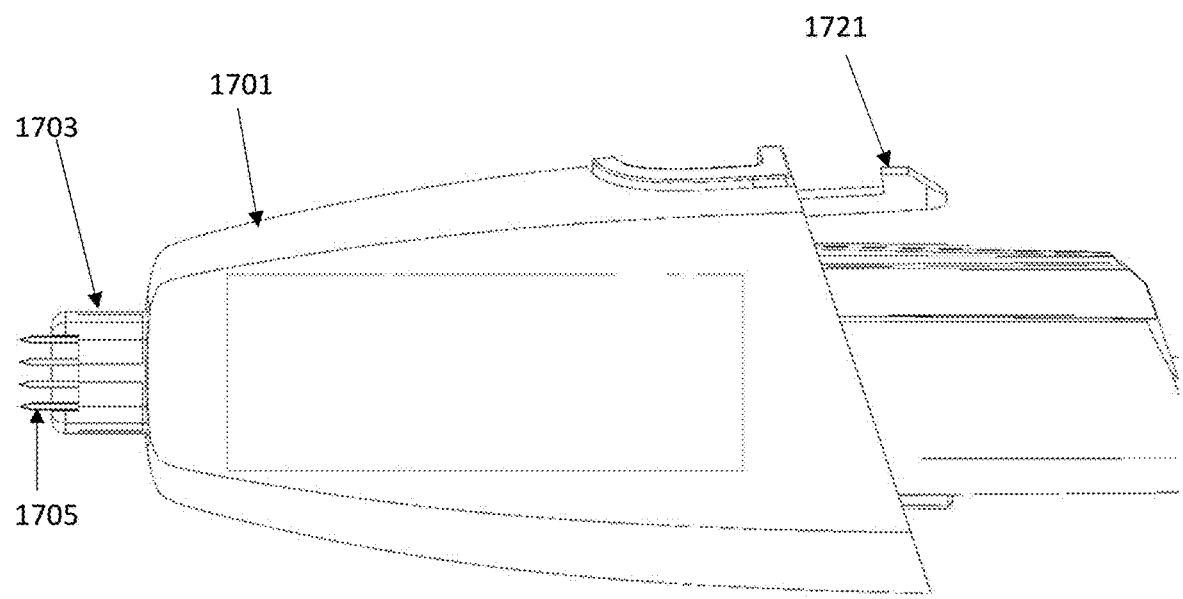
Figure 18A:
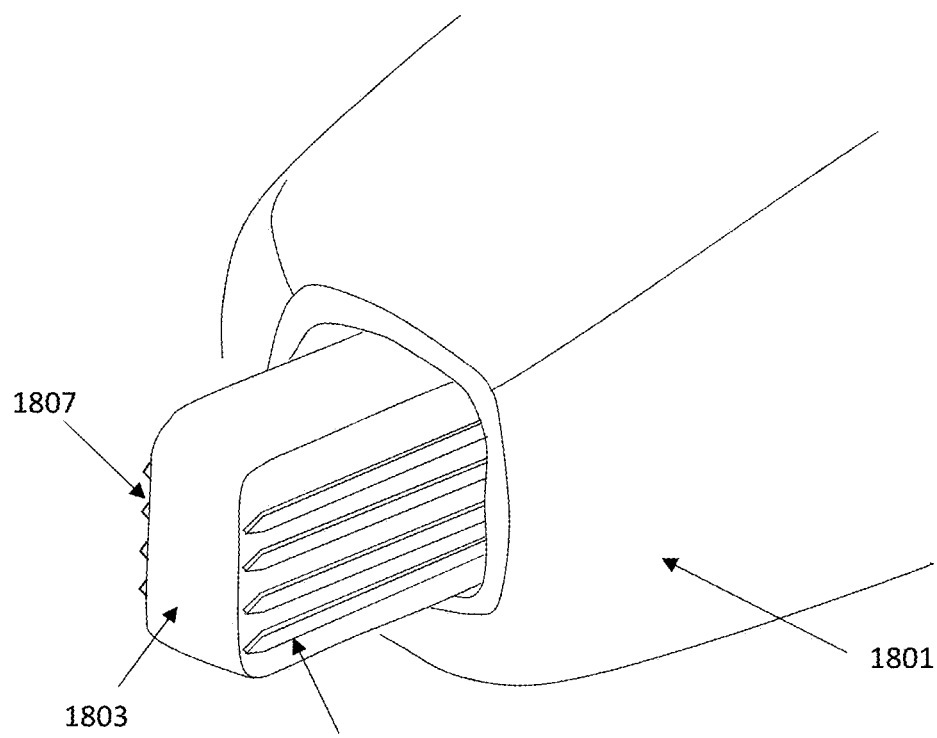
FIGS. 18A and 18B show examples of a front perspective view of another variation of a distal end face of a retractable treatment tip device.
Figure 18B:
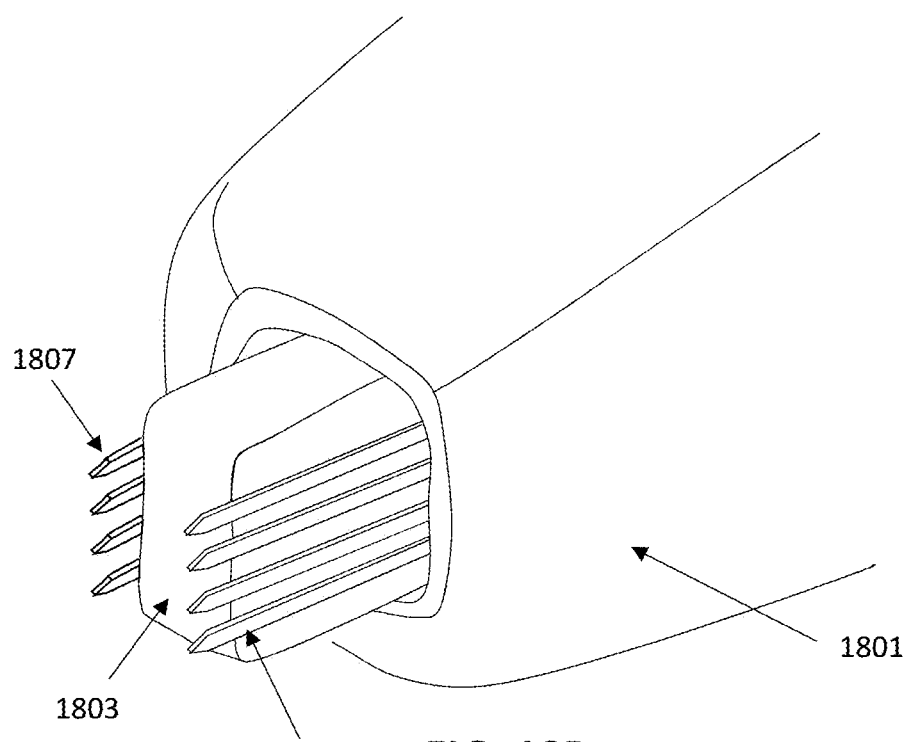

FIGS. 17C and 17D show side views of the device of FIGS. 17A and 17B with the electrode partition 1703 in the un-deployed (FIG. 17C) and deployed (FIG. 17D) configurations, respectively. As described above, the treatment tip housing 1701 may include a mechanical connector 1721 (shown by example as a snap or latch) that couples the retractable treatment tip to a handle. The retractable treatment tip also includes two or more electrical connectors (not visible in FIGS. 17A-17D) for coupling the electrodes 1705, 1707 to the controller and/or power supply.

FIGS. 18A-18B show another example of a treatment tip device for delivery of electrical therapy in which the electrode partition 1803 is retractable into the treatment tip housing 1801 (shown in FIG. 18B). In this example the electrode partition does not enclose the electrodes even partially, but extends between the first set (e.g., of one or more electrodes) 1805 and the second set (e.g., of one or more electrodes) 1807, and may insulate them from each other and prevent or limit arcing. In this example, the lateral windows or cut outs extend completely along the length of the electrode partition into the treatment tip housing, or these lateral regions may be missing entirely, so that the first and second sets of electrodes extend on either sides of the electrode partition. In some variations the electrode partition may partially enclose the first and second sets of electrodes, e.g., curving around (and in some variations between) them. For example, the electrode partition may have an I-shaped cross-section, in which the top and bottom of the "I" shape extend partially around the sides of the first and second sets of electrodes, leaving the lateral, outward-facing sides open.

In any of the exemplary electrode partitions shown in FIGS. 17A-18B, the lateral openings (e.g., lateral windows), may be referred to as lateral cut-out regions from the electrode partition and may allow visualization of the electrodes even in the un-deployed configurations, so that the electrodes may be visualized before or during deployment. This may aid the user in targeting a tissue (e.g., a lesion) to be treated, including positioning the target tissue between the electrodes (e.g., in between two rows of needles for the variations shown in FIGS. 17A-18B). This configuration may also allow the user to verify the orientation of the electrodes.

Figure 19:
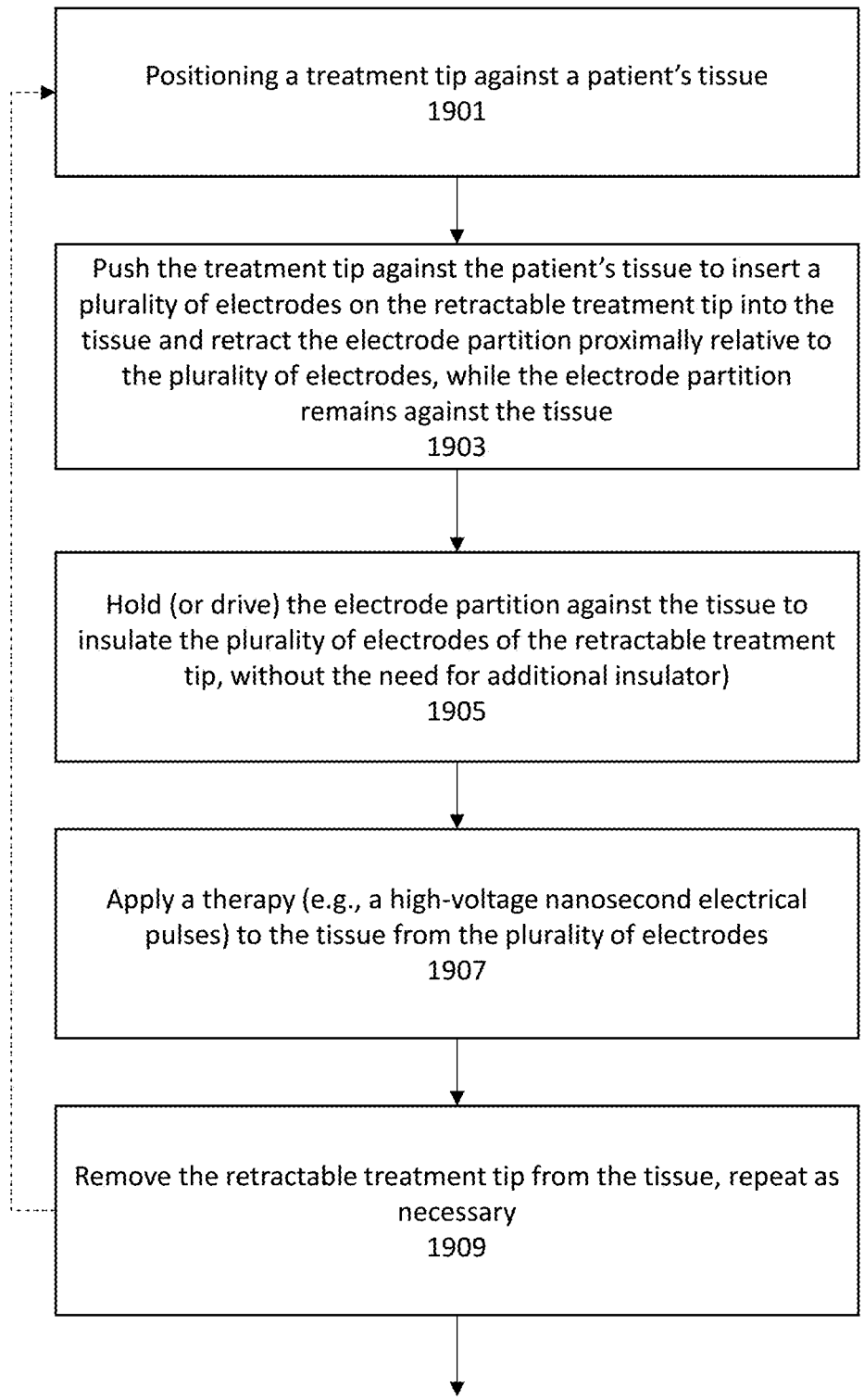
FIG. 19 is a schematic diagram illustrating an example of a method of applying high-voltage nanosecond pulse electrical therapy as described herein.

FIG. 19 illustrates a flowchart of an example of a general method of treatment. In FIG. 19, the method is a method of, e.g., applying high-voltage nanosecond pulse electrical therapy to treat a subject. The method may include, as a preliminary step 1901, initially positioning a retractable treatment tip against a subject's tissue. In step 1903, a plurality of electrodes of a retractable treatment tip are inserted into the tissue (out and past the distal face of the electrode partition) while the electrode partition is retracted into the tip housing. In some embodiments the treatment tip device may be pushed against the subject's tissue with a force that is greater than a threshold force necessary to retract the electrode partition proximally relative to the plurality of electrodes while penetrating the tissue with the plurality of electrodes. When bias is present, the applied driving force may overcome the bias (the threshold force). The electrode partition (e.g., housing) may be driven against the tissue to help electrically isolate the plurality of electrodes from each other. Alternatively or additionally, the tissue-penetrating (e.g., needle) electrodes may be deployed by releasing a bias (or by applying a force greater than the threshold force set by the bias) to drive the electrode distally relative to the distal face of the electrode partition, so that they penetrate the tissue and simultaneously drive the distal face of the electrode partition against the tissue.

In general, the retractable treatment tip may be any of the applicator tips (treatment tips) described herein, particularly those including an electrode partition (or electrode housing) extending from a distal end of a treatment tip housing. The retractable treatment tip may also comprise a bias, for example, a bias holding and in some variations driving the electrode partition distally with a bias return force, and a plurality of treatment electrodes at least partially within the electrode partition. The retractable treatment tip may also comprise an insulator, for example, a distal insulating cover covering the electrodes within the electrode partition. In step 1905 (which may occur, for example, simultaneously with the step 1903), the plurality of electrodes are insulated against the tissue. In some embodiments, the electrodes may be insulated with the use of an insulator (e.g., insulating cover, or insulating material), or with the use of one or more vacuum ports, or both.

Once the treatment electrodes are inserted into the tissue (e.g., skin) to the desired depth, including fully deployed as limited by the full retraction position of the electrode partition, in step 1907 a therapy, such as electrical energy therapy, may be applied to the tissue. For example, high-voltage nanosecond electrical pulses may be applied to the tissue from the plurality of electrodes. As mentioned above, the step of applying energy may be done without the need for any additional insulator or insulating material (e.g., gel) between the applicator tip and the tissue. Upon completion of the application of energy, in step 1909 the tip may be removed from the tissue (e.g., by withdrawing the applicator tip). If there are additional regions to be treated, the applicator tip may be removed to the new location, typically on the same person, or they may be completely removed.

Figure 20B:
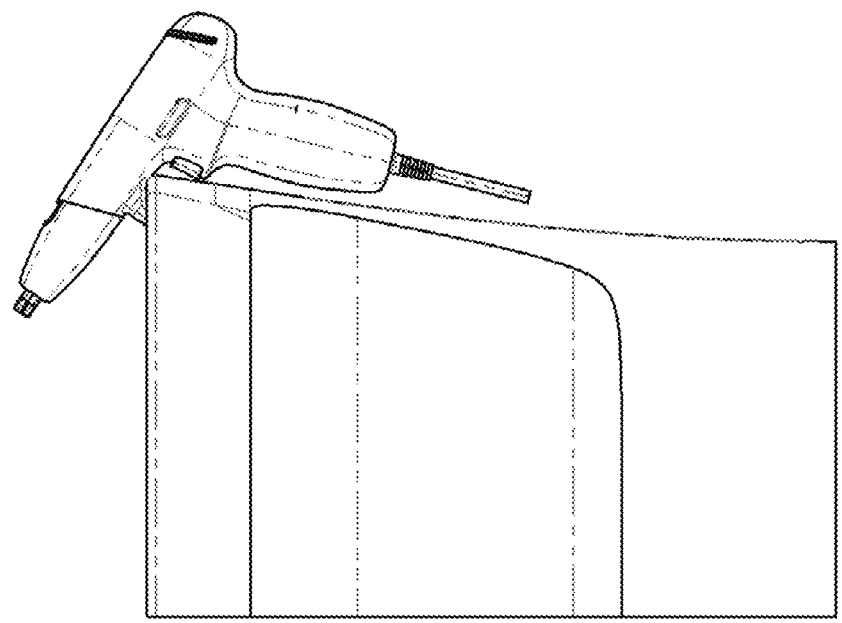
FIGS. 20A-20B illustrate an example of an applicator handle that is configured as a gun and is configured for easy storage on a rim of a tray or other holder.
Figure 20A:
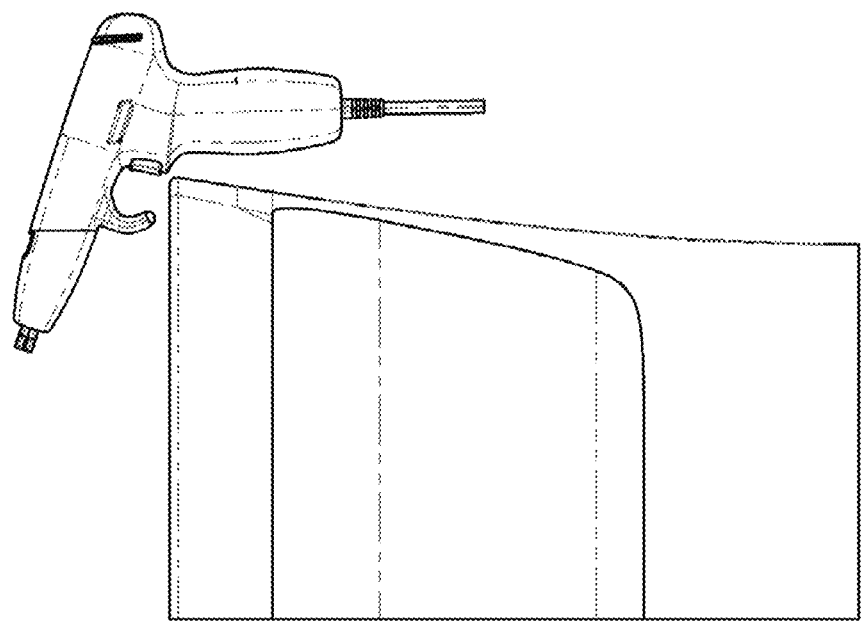

Also described herein are hooks, latches, and holsters for the reusable component (e.g., handle such as a gun or other form factor that may be used to hold the applicator (with or without the treatment tips described herein). For example, FIGS. 20A and 20B illustrate the temporary attachment of an applicator gun for use with the applicator tips described herein. In this example the reusable applicator is secured over a lip or edge by an attachment site on the applicator. FIG. 20B shows the apparatus of FIG. 20A coupled to a lip or edge.

Figure 21A:
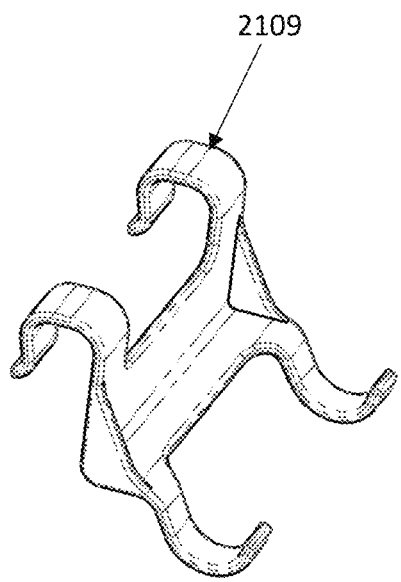
FIGS. 21A-21C illustrates an example of a holster accessory device for use with some examples of an applicator apparatus such as shown in FIGS. 20A-B.
Figure 21B:
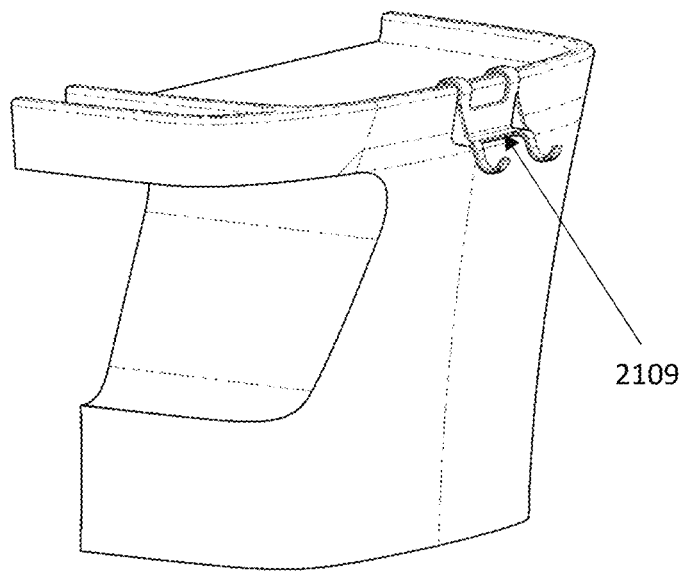
Figure 21C:
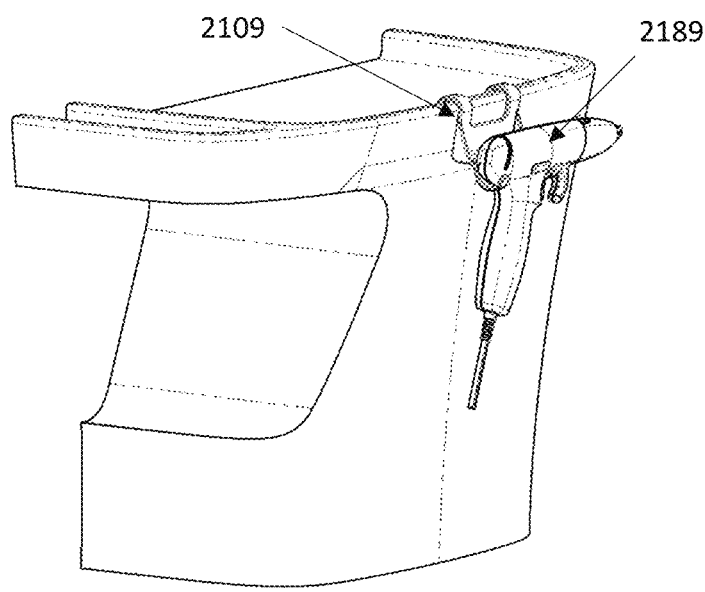

In some variations an additional hook or tool, such as the hook shown in FIG. 21A, may be used as an intermediate between the reusable handle and an edge or other exposed outer surface, e.g., or an operating table or the like. A longer version of the hook may be used as a holster for the gun applicator (or other shapes/configurations of the applicator tip and applicator housing, as shown in FIGS. 21B and 21C. In FIG. 21B, the hook 2109 is attached over a lip of a surgical tray or cart, including a cart holding the rest of the applicator system. In FIG. 21C, the hook 2109 is shown attached onto a tray or table edge and the applicator handle 2189 is held within the hook.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating a subject, the method comprising:
    placing an electrode housing of a treatment applicator adjacent to the subject's tissue, wherein the treatment applicator is in an un-deployed configuration, in which distal ends of a plurality of treatment electrodes are housed within the electrode housing and do not extend beyond a soft, electrically insulating distal end of the electrode housing;
    driving the electrode housing of the treatment applicator against the subject's tissue to convert the treatment applicator to a deployed configuration in which the electrically insulated distal end of the electrode housing retracts proximally relative to the plurality of treatment electrodes and the plurality of treatment electrodes extends beyond the soft, electrically insulating distal end of the electrode housing and into the subject's tissue; and
    holding the soft, electrically insulating distal end of the electrode housing against the subject's tissue to prevent arcing between the plurality of treatment electrodes when energy is applied to the subject's tissue from the plurality of treatment electrodes.

2. The method of claim 1, further comprising applying energy to the subject's tissue from the plurality of treatment electrodes.

3. The method of claim 2, wherein applying energy comprises applying a sub-microsecond pulsed electric field.

4. The method of claim 1, wherein at least one electrode of the plurality of electrodes has an insulated portion and a distal uninsulated end, the method further comprising setting or adjusting a length of the insulated portion of the at least one electrode.

5. The method of claim 4, wherein the distal uninsulated end of the at least one electrode is between 0 mm and 20 mm.

6. The method of claim 1, wherein placing the electrode housing of the treatment applicator adjacent to the subject's tissue comprises positioning the treatment applicator against subject's skin.

7. The method of claim 1, further comprising releasing a release lock to allow the electrode housing to be retracted proximally into a treatment tip housing of the treatment applicator.

8. The method of claim 1, wherein driving the treatment applicator against the subject's tissue comprises driving the treatment applicator with a force that is greater than a threshold force necessary to overcome a bias holding the electrode housing extended from a treatment tip housing of the treatment applicator in the un-deployed configuration.

9. The method of claim 1, wherein placing the electrode housing of the treatment applicator adjacent to the subject's tissue comprises placing the electrode housing adjacent to one or more of: a malignant tumor or lesion of any stage and grade, a benign tumor or lesion, and a pre-cancerous tumor or lesion.

10. The method of claim 1, further comprising applying sub-microsecond electric pulses from the plurality of treatment electrodes to treat at least one of the following: digestive and gastrointestinal cancers, colorectal cancer, gastrointestinal stromal tumors, gastrointestinal carcinoid tumors, colon cancer, rectal cancer, anal cancer, bile duct cancer, small intestine cancer, esophageal cancer; breast cancer, lung cancer, gallbladder cancer, liver cancer, pancreatic cancer, appendix cancer, prostate cancer, ovarian cancer, renal cell carcinoma, cancer of the central nervous system, skin cancer, lymphomas, gliomas, choriocarcinomas, head and neck cancers, osteogenic sarcomas, blood cancer, and Kaposi's sarcoma.

11. The method of claim 1, further comprising applying sub-microsecond electric pulses from the plurality of treatment electrodes to treat at least one of: skin lesions, aging skin, skin tumors, acne, seborrheic keratosis, keloids, scars, molluscum contagiosum, acrochordon, psoriasis, papilloma, human papilloma virus (HPV), melanoma, melasma, sebaceous hyperplasia (SH), syringoma, congenital capillary malformation (port-wine stains), congenital nevi, actinic keratosis, dermatosis papulosa nigra, angiofibroma, cherry angioma, warts, molluscum angioma, necrobiosis lipoidica (NBL), melisma, lipoma epidermal/sebaceous cyst, and basal cell carcinoma.

12. The method of claim 1, further comprising applying sub-microsecond electric pulses from the plurality of treatment electrodes to treat at least one of the following cosmetic treatments: tattoo removal, hair follicle destruction, aging skin, scar/keloids reduction, fat reduction, and wrinkle reduction.

13. The method of claim 1, further comprising setting a length of the plurality of treatment electrodes prior to driving the soft, electrically insulating distal end of the electrode housing against the subject's tissue.

14. The method of claim 1, wherein a material of the soft, electrically insulating distal end of the electrode housing has a durometer of 60 or less on the Shore A hardness scale.

15. The method of claim 1, wherein the soft, electrically insulating distal end of the electrode housing extends at least partially down a side of the electrode housing.

16. The method of claim 1, wherein the soft, electrically insulating distal end of the electrode housing comprises one or more of: silicon, santoprene, or other TPE (Thermoplastic Elastomer) materials.

17. The method of claim 1, further comprising adjusting a distal-to-proximal length of the plurality of treatment electrodes, wherein the adjusting is done with a lever, a dial, a slider, a knob, a button, a screw mechanism or a cam assembly.

18. The method of claim 1, wherein the plurality of treatment electrodes comprises needle electrodes.

19. The method of claim 1, further comprising releasably coupling the treatment applicator to a handle.

20. A method of treating a subject, the method comprising:
    positioning an electrode housing of a treatment tip against the subject's tissue, wherein the treatment tip comprises a bias applying force against the electrode housing extending from a distal end of a treatment tip housing, the electrode housing having a soft, electrically insulting distal end and a plurality of needle electrodes within the electrode housing, further wherein the treatment tip is in an un-deployed configuration in which the electrode housing extends over the plurality of needle electrodes;

deploying the treatment tip by driving the electrically insulated distal end of the electrode housing against the subject's tissue so that the electrode housing is retracted into the treatment tip housing against the bias while the plurality of needle electrodes are inserted into the subject's tissue, wherein the soft, electrically insulating distal end is applied against the subject's tissue to electrically isolate the plurality of needle electrodes and prevent or reduce arcing; and applying energy to the subject's tissue from the plurality of needle electrodes.

21. A method of treating a subject, the method comprising:

positioning an electrode housing of a treatment tip adjacent to the subject's tissue, wherein the electrode housing extends from a distal end of a treatment tip housing and a bias applies a bias force to hold the electrode housing extended from the treatment tip housing and over a plurality of needle electrodes within the electrode housing, the electrode housing including a soft, electrically insulating distal end having a durometer of 60 or less on the Shore A hardness scale;

pushing the treatment tip against the subject's tissue with a force that is greater than the bias force to drive the electrode housing proximally relative to the plurality of needle electrodes while penetrating the subject's tissue with the plurality of needle electrodes; and applying nanosecond electrical pulses to the subject's tissue from the plurality of needle electrodes while holding the soft, electrically insulating distal end against the subject's tissue to electrically isolate the plurality of needle electrodes and prevent or reduce arcing.

22. The method of claim 1, the method comprising customizing a depth of tissue penetration by the plurality of electrodes thereby customizing a depth of a lesion being treated.

* * * * *